United States Patent [19]

Williams, II et al.

[11] Patent Number: 4,910,463
[45] Date of Patent: Mar. 20, 1990

[54] HALOGEN MONITORING APPARATUS

[75] Inventors: William J. Williams, II, Ft. Myers Beach; Daniel M. Thorsen, Clearwater, both of Fla.

[73] Assignee: Sentech Corporation, Indianapolis, Ind.

[21] Appl. No.: 134,293

[22] Filed: Dec. 17, 1987

[51] Int. Cl.[4] ............................................ G01N 27/62
[52] U.S. Cl. ...................................... 324/468; 324/464
[58] Field of Search ............... 324/464, 468, 470, 438, 324/459; 250/382, 379, 388; 73/26

[56] References Cited

U.S. PATENT DOCUMENTS

| | | |
|---|---|---|
| 2,795,716 | 6/1957 | Roberts . |
| 2,806,991 | 9/1957 | White . |
| 2,996,661 | 8/1961 | Roberts . |
| 3,009,074 | 11/1961 | Roberts . |
| 3,065,411 | 11/1962 | Roberts . |
| 3,071,722 | 1/1963 | Roberts . |
| 3,076,139 | 1/1963 | Roberts . |
| 3,144,600 | 8/1964 | Roberts . |
| 3,363,451 | 1/1968 | Roberts . |
| 3,439,262 | 4/1969 | Roberts . |
| 3,471,746 | 10/1969 | Roberts . |
| 3,617,734 | 11/1971 | Chaudet et al. . |
| 3,728,615 | 4/1973 | Hill et al. ............................ 324/464 |
| 3,739,260 | 6/1973 | Schadler . |
| 3,875,499 | 4/1975 | Roberts . |
| 3,912,967 | 10/1975 | Longenecker . |
| 3,991,360 | 11/1976 | Orth et al. . |
| 4,047,101 | 9/1977 | Bauerle et al. . |
| 4,053,825 | 10/1977 | Young . |
| 4,129,418 | 12/1978 | Davis . |
| 4,151,641 | 5/1979 | Mitoff . |
| 4,157,311 | 6/1979 | Orth et al. . |
| 4,164,861 | 8/1979 | Schlereth et al. . |
| 4,196,427 | 4/1980 | Rudberg . |
| 4,205,249 | 5/1980 | Davis . |
| 4,282,741 | 8/1981 | Zarchy . |
| 4,366,438 | 12/1982 | Ibe et al. . |
| 4,488,118 | 12/1984 | Jeffers et al. . |
| 4,609,875 | 9/1986 | Jeffers . |
| 4,714,891 | 12/1987 | Morrison, Jr. ...................... 324/459 |

Primary Examiner—Reinhard J. Eisenzopf
Assistant Examiner—Jack B. Harvey
Attorney, Agent, or Firm—Neuman, Williams, Anderson & Olson

[57] ABSTRACT

An apparatus for monitoring the concentration levels of halogen gas in a gaseous atmosphere as confined in an enclosure over a relatively extended period of time. Such monitoring apparatus includes a sensor including first and second electrodes disposed to define a space therebetween through which the gaseous atmosphere flows and a voltage source for applying a voltage between the first and second electrodes whereby an ionization current flows to the first electrode. A control mechanism illustratively in the form of a programmed microcontroller monitors the ionization current collected by the first electrode as the output signal of the sensor, to determine an increase therein as would be indicative of a halogen leak. Upon determining an increase of the sensor output signal above a predetermined difference, the control mechanism removes the energization from the halogen sensor whereby the ionization current is terminated and the life of the sensor extended. The control mechanism further causes an initial reading of the sensor signal to be taken and to be stored, whereby subsequent sensor readings may be compensated by subtracting the stored value therefrom to provide a compensated output indicative of the increased halogen level with respect to the initial background reading thereof. The relatively small halogen sensor output is amplified by a variable gain amplifier.

28 Claims, 11 Drawing Sheets

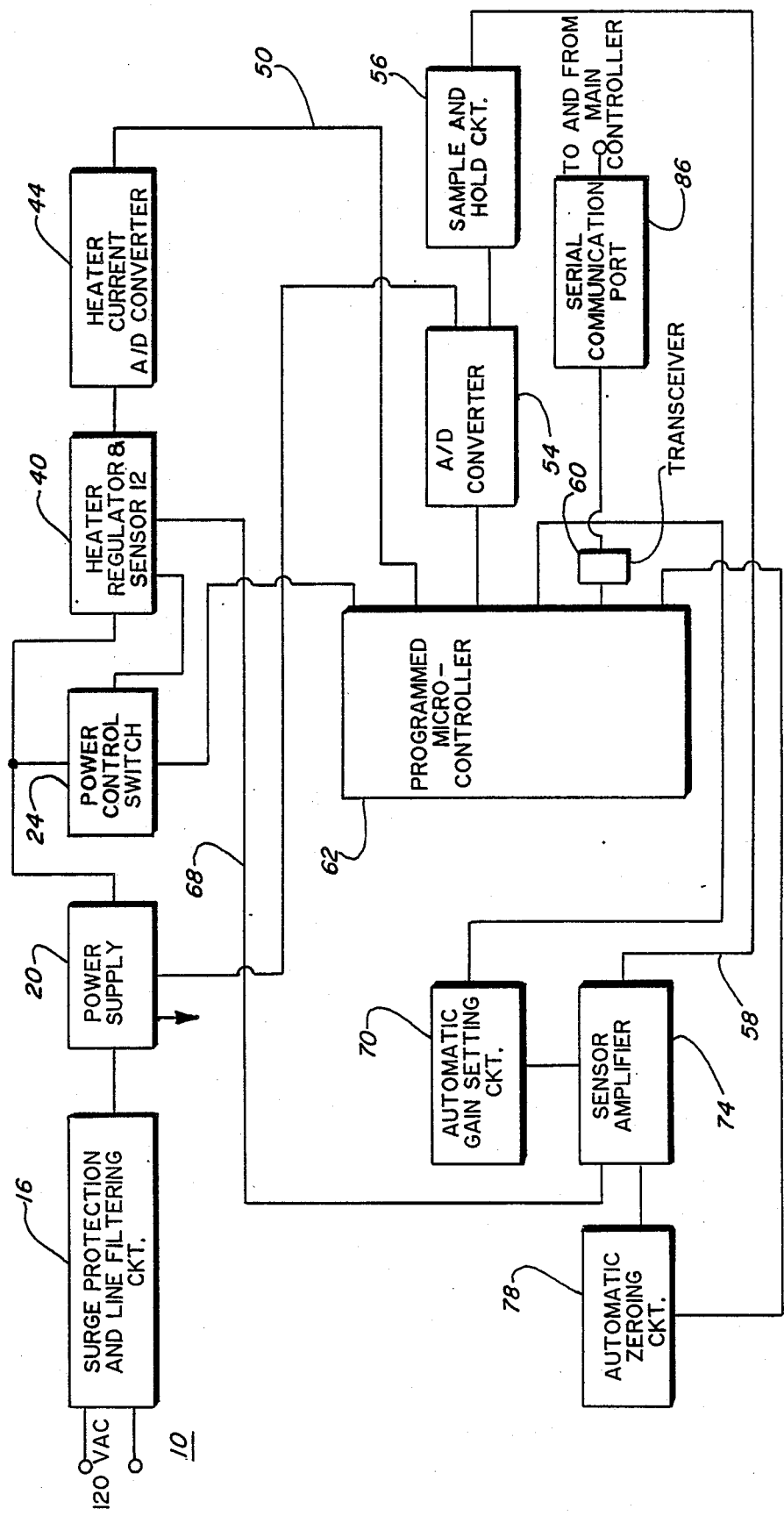
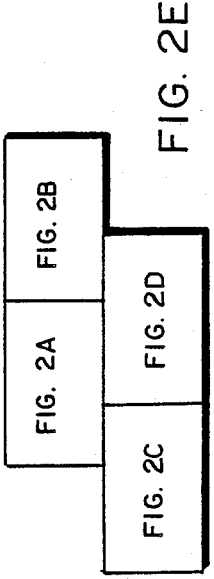
FIG. 1
FIG. 2E

HALOGEN MONITORING APPARATUS

FIELD OF THE INVENTION

This invention relates to halogen gas monitors and, in particular, to apparatus including halogen gas sensors for processing the sensor output signal to determine the existence of a halogen leak with greater reliability over an extended period to time.

DESCRIPTION OF THE PRIOR ART

Sensors such as that described in U.S. Pat. No. 2,550,498 of Rice take the form of an electrical discharge device for receiving a sample of an atmosphere suspected of containing a concentration of a substance to be detected and comprising cathode and anode elements for producing and collecting ions. The collected ions produce from one of these electrodes a current which varies with the concentration of the substance to be detected.

One common use of such electrical discharge devices is as sensors within halogen leak detectors to detect the leakage of halogens and their gas compounds. In order to detect widely varying levels of concentration of such substances, the prior art halogen leak detectors have included provisions for adjusting the sensitivity of the sensor in order to extend the useful range. Such detectors have ranges of sensitivity which limit their use to the detection of leak rates within a limited span of leak rates. Thus, a halogen leak detector having a sensitivity adapted for measuring relatively large leak rates of halogen compounds on the order of $10^{-3}$ cc./sec. into a particular region, could be altered only with difficulty to increase its sensitivity so as to detect accurately leak rates of halogen compounds on the $10^{-9}$ cc./sec. into the same region. Typically, halogen leak detectors have marginal stability when operating near the upper limits of their sensitivity as evidenced by fluctuations in their output readings.

Many prior art halogen leak detectors are portable and are carried to particular site where a leak of a relatively high level of concentration of halogens was suspected to be present. However, applications have arisen such as in the refrigeration industry where it is desired to monitor low rate halogen leaks into relatively large enclosures. Typically, the levels of halogen concentration in such relatively large enclosures are quite small, requiring extremely sensitive and stable leak detectors.

U.S. Pat. No. 3,144,600 of Roberts discloses a halogen leak detector comprising an electrical discharge device as its sensor and employing an amplifier of variable gain for amplifying the output current of the sensor. In particular, the gain of the amplifier is set by a multi-range control switch to adapt the sensor for sensing corresponding multiple ranges of levels of halogen concentration. In addition, the collected current as produced by the sensor in the presence of clean air is compensated by applying an adjustable zeroing voltage of opposite polarity to the output current of the sensor. More particularly, the magnitude of the zeroing voltage is adjusted over a range sufficient to null the sensor output even when it is operating in its highest range of sensitivity, i.e. when the multi-range control switch is adjusted to impart the least degree of attenuation so as to sense relatively small concentrations of halogen compounds.

U.S. Pat. Nos. 2,996,661 of Roberts discloses the adjustment of leak detectors for varying levels of concentration by controlling the flow of the atmosphere to the detector through use of a variable orifice. U.S. Pat. No. 3,875,499 of Roberts discloses the use of such a variable orifice in combination with a combined multi-range switch as would affect the gain of a sensor output amplifier and also would variably set a selected orifice to permit a corresponding flow to the sensor.

U.S. Pat. No. 3,065,411 of Roberts further discloses a halogen leak detector capable of indicating both the current level and the relative magnitude of the change in the detected concentration of halogen compounds. A first circuit is responsive to the collected current to be set into damped oscillation by a change of the collected current. The damped oscillation is in turn applied to a control circuit having a threshold level. Oscillation above that threshold level will dispose the control circuit to its conducting condition. Further, the first circuit includes means for changing the amplitude of the oscillations in order to accommodate sensing halogen compounds of varying concentrations.

U.S. Pat. No. 3,076,139 of Roberts relates to a halogen leak detector particularly adapted to sense changing concentrations of halogen compounds, as well as to respond only to sudden changes in the level of halogen concentration. An RC coupling circuit is connected between a sensor as described above and an amplifier, which drives a leak indicating means. The RC coupling circuit repeatedly discharges its input signal, zeroing in effect the sensor and permitting a new sensing of the halogen compounds. A multi-position switch is provided to connect a selected capacitor from a plurality of available capacitors to form a corresponding RC coupling circuit for each of the plurality of ranges of halogen concentration to be sensed.

U.S. Pat. No. 3,363,451 of Roberts discloses a halogen leak detector wherein a capacitor is charged by a variable biasing circuit and a current derived from its sensor to the level of the detected halogen concentration. The capacitor is in turn connected to a control circuit having a threshold level, which may be exceeded by the output of the charged capacitor to energize a leak indicating means. The variable biasing circuit includes a potentiometer which is adjusted in accordance with the desired range of halogen concentration to be detected. A further sensitivity switch is provided to couple a battery to extend the range of balance control of the potentiometer in order to accommodate higher levels of current and thus higher levels of halogen concentration.

As evident from the above discussion of the prior art, such halogen leak detectors were primarily portable devices not particularly adapted for extended monitoring applications of a single environment, where it would be particularly desired to sense relatively low levels of halogen concentration. It was contemplated that such portable detectors would be used with an operator continually present to set the desired range of halogen concentration to be detected by manipulating a multi-range switch, while observing a suitable leak detecting means such as a meter. When a suitable mid-range indication was provided on the meter, the operator knew that the correct switch setting had been achieved. Such a portable halogen leak detector is described in a service manual entitled "The Ferret ® Leak Detector (type H25)" published by General Electric. The H25 leak detector uses an integrator to continually eliminate background steady-state signals from its sensor. In an application of extended use of a halogen leak detector as is contemplated by this invention, such an integrator type of circuitry would continually zero any small incremental leaks in a particular enclosure and would not be able to sense the accumulation of such small leaks.

The halogen sensors in the form of an electrical discharge device are relatively expensive. The life of such sensors is relatively limited requiring frequent replacement. Experience with that halogen sensor manufactured by Yokagowa Corp. under model No. 66l4K11G1 has shown it to have a life of approximately 1500-1800 hours. The collector/cathode elements of such electrical discharge devices are coated with rare earth metals and tend to deteriorate rapidly during sustained collection of the ion stream as occurs in the presence of halogen gases. In applications wherein such a halogen sensor and its leak detector are used to monitor halogen leaks within a given enclosure for relatively long periods of time, a halogen leak may occur and is accordingly sensed by the halogen sensor for a relatively long period of time until an operator may intervene to re-set, re-zero or otherwise disable the halogen sensor. During such a relatively long period, the collector/cathode element of the sensor is continually bombarded by the increasing level of ions due to the presence of the halogen. Such extended use quickens the deterioration of the collector/cathode elements and therefore the life of such halogen sensors.

SUMMARY OF THE INVENTION

It is therefore an object of this invention to provide a new and improved halogen monitoring apparatus as is capable of automatic operation without operator intervention, thus permitting this apparatus to be used unattended to monitor halogen leaks in a particular enclosure for extended periods of time.

It is a further object of this invention to provide a new and improved halogen monitoring apparatus for the sensing of halogen leaks in which the life of its halogen sensor is significantly extended.

It is another object of this invention to provide a new and improved regulating circuit for a halogen sensor, which is capable of compensating for residual levels of halogen in a particular enclosure.

It is a still further object of this invention to provide a new and improved halogen monitoring apparatus which is capable of initially taking a reading of the residual or initial level of halogen within a particular enclosure and of compensating or subtracting that level from further halogen measurements.

It is a still further object of this invention to provide a new and improved halogen monitoring apparatus which is capable of automatically setting the sensitivity level of its sensor in a selected range from a plurality of such ranges.

It is another object of this invention to provide a new and improved halogen monitoring apparatus which is capable of providing a leak manifestation indicative of a selected increase in the level of halogen concentration.

In accordance with these and other objects of this invention, there is disclosed halogen monitoring apparatus including a halogen sensor of the type described with first and second electrodes disposed to define a space therebetween through which a gaseous atmosphere to be monitored flows, and a voltage source coupled to apply a voltage across the first and second electrodes, whereby an ionization current flows between the electrodes. The life of the sensor is extended by a control circuit as illustratively includes a programmed microcontroller for sensing an increase in the ionization current and, if greater than a selected level, for causing the voltage source to remove or reduce the voltage therebetween to terminate the ionization current flow and thus extend the life of the halogen sensor.

In a further aspect of this invention, the halogen monitoring apparatus includes a memory and a control mechanism illustratively in the form of a programmed microcontroller for initially taking a first reading of the sensor signal as is indicative of a background or steady state level of the halogen gas within an enclosure to be monitored and for storing that background level signal in the memory to be used as a compensating signal to be subtracted from further readings of the sensor signal to provide a compensated value indicative of the increase in the level of halogen concentration within the monitored enclosure.

In a still further aspect of this invention, the amplitude of the sensor signal is relatively low and is amplified by a variable gain sensor amplifier. The gain of the sensor amplifier is set by initially setting the gain to a relatively low value and thereafter increasing it until the output of the amplifier reaches a predetermined level and, thereafter, decreasing the amplifier gain.

In an illustrative embodiment of this invention wherein the control of the halogen monitoring apparatus is carried out by a programmed microcontroller, the apparatus includes an analog-to-digital (A/D) converter coupled to receive the output of the sensor amplifier. When the A/D converter overflows, the gain of the sensor amplifier is reduced a discreet amount or to the next lower setting, whereby the output of the A/D converter is set at a mid-level output.

In a further aspect of this invention, the halogen monitoring apparatus provides an indication of a halogen leak by determining an increase in the level of halogen concentration. In particular, an increase in the gain of the sensor amplifier as well as an increase in the sensor signal are determined and if greater than a predetermined difference or increase, there is an indication of a leak. The monitoring apparatus may be set to measure a selected one of a range of halogen increases or differences, whereby the sensitivity of the monitoring apparatus may be correspondingly set.

BRIEF DESCRIPTION OF THE DRAWINGS

These and other objects and advantages of the present invention will become apparent by referring to the following detailed description and accompanying drawings, in which:

FIG. 1 is a diagrammatic drawing of a halogen monitoring apparatus in accordance with teachings of this invention;

FIGS. 3A to 3F are flow diagrams of the program executed by that microcontroller as shown in FIG. 2D.

DESCRIPTION OF THE PREFERRED EMBODIMENT

Figure 2A:
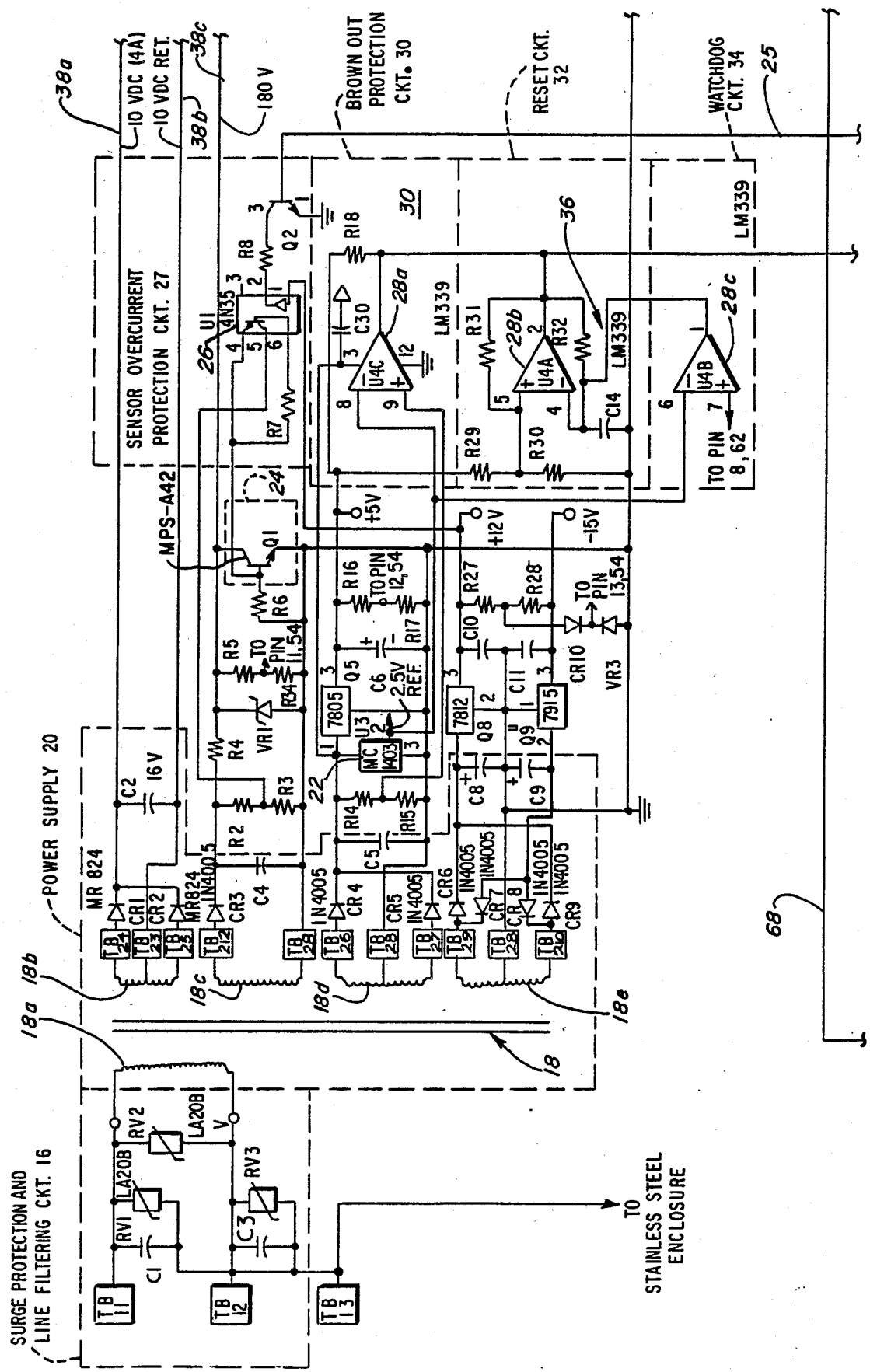
FIGS. 2A to 2D, when assembled as shown in FIG. 2E, are detailed schematic drawing of the halogen monitoring apparatus as shown in FIG. 1

With reference to the drawings and in particular to FIG. 1, there is shown a halogen monitoring apparatus 10, particularly adapted to monitor the atmosphere within an enclosure to detect the occurrence of halogen leaks in accordance with the teachings of this invention. The monitoring apparatus 10 of this invention differs from the prior art which is typically a portable device as is brought to a particular area where a leak is suspected. In an illustrative use of this invention, the halogen monitoring apparatus 10 is disposed in an enclosure where there are disposed a number of compressors of the type as used for large, commercial refrigerators. Such compressors leak at low rates their refrigerant which comprises halogens or compounds thereof. If the leaks continue over a long period of time, a considerable amount of the refrigerant will be lost. The refrigerant is expensive, and there may be also spoilage of the refrigerated product, e.g., food. The halogen monitoring apparatus 10 of this invention is particularly adapted to monitor such environments and, in particular, for sensing relatively small concentrations of, or leak rates of halogen gases. If the source of the halogen leaks, e.g., compressors, is disposed in an enclosure with a relatively efficient flow of air therethrough, as would tend to dissipate the leaked halogen, the halogen monitoring apparatus 10 would in effect monitor the leak rate. On the other hand, if the enclosure is sealed, the leaked halogen would tend to build up and the halogen monitoring apparatus 10 would tend to provide an indication of the accumulated concentration of halogen leaked into such a sealed enclosure. As will be explained, the halogen monitoring apparatus 10 is capable for operation over relatively long periods of time, if not continuous operation, whereby halogen leaks are immediately detected so that appropriate remedial steps may be taken quickly to repair immediately the leaking compressors.

As shown in FIG. 1, the halogen monitoring apparatus 10 includes a heater regulator 40, which in turn comprises a halogen sensor 12, adapted and operated to detect halogen leaks in accordance with the teachings of this invention. The halogen sensor 12 is shown in detail in FIG. 2B as including a heater/anode element 13 and a collector/cathode element 14 spaced therefrom and enclosed by an electrical shield 15. In an illustrative embodiment of this invention, the halogen sensor 12 may take the form of that sensor manufactured by Yokagowa Corp. under their designation 66l4K11G1. The collector/cathode element 14 thereof illustratively takes the form of a rod suspended in a powdered-alkali metal core housed in a concentric platinum tube. The tube and rod are connected by a welded platinum strip, thus keeping rod and tube at the same potential. The heater/anode element 13 may illustratively take the form of a coiled-wire heater wrapped on four ceramic posts and disposed about the aforementioned rod/tube assembly. Illustratively, a voltage in the order of 180 volts is imposed between the heater/anode element 13 and its collector/cathode element 14. Approximately 10 volts is applied across the heater/anode element 13, whereby current in the order of 4 amps is directed therethrough and the temperature of the sensor 12 is raised to approximately 900° C., causing a small current to flow in the rod of the collector/cathode element 14. This small current flow, which is due to ionization of the core material, increases linearly to a useful limit proportioned to the level of halogen in the gas or gaseous atmosphere passing through the sensor 12. Beyond this limit, the increase in current is extremely non-linear and excessive increases in halogen in the circulated atmosphere only serve to shorten the life of the halogen sensor 12. The current collected in the collector/cathode element 14 and appearing as an output signal of the halogen sensor 12 on a sensed current line 68 is rather small being in the order of 1–100 $\mu A$.

Referring now to FIG. 1, the collected current in the collector/cathode element 14 (see FIG. 2B) provides the output signal of the halogen sensor 12 (and its heater regulator 40) and is applied via the sensed current line 68 to a sensor amplifier 74, which amplifies the sensor signal and applies same via an output line 58 to a sample and hold circuit 56. In turn, the sensor signal in an analog form is applied to an analog-to-digital (A/D) converter 54, which converts and applies the digital sensor signal to the microcontroller 62. The gain of the sensor amplifier 74 may be varied by an automatic gain setting circuit 70 and, in particular, set at a selected one of a plurality of gain or tap settings, corresponding to various ranges of sensitivity of the sensor 12. As illustrated in FIG. 1, the gain setting of the circuit 70 is controlled by the programmed microcontroller 62.

As shown in FIG. 1, power is supplied to the heater regulator circuit 40 and its sensor 12 by a power supply 20. In turn, a typically available 120 VAC is applied to a surge protection and line filtering circuit 16, which in turn energizes the power supply 20. The various operations and functions of the halogen monitoring apparatus 10 are controlled by a programmed microcontroller 62, the program being illustrated in FIGS. 3A to 3F. In particular, the programmed microcontroller 62 senses an output from the sensor 12 indicative of the presence of a certain level of halogen gas. When a halogen leak has been detected, the microcontroller 62 closes a power control switch 24 to thereby shortout the 180 volts provided by the power supply 20 and to remove the heater/anode supply voltage from the sensor 12. As will be explained in detail later, the removal of the heater/anode supply voltage from the sensor 12 prevents the rapid deterioration of its collector/cathode element 14 due to the ion bombardment that occurs in the presence of halogens, whereby the life of the sensor 12 is significantly prolonged. As a result, the halogen monitoring apparatus 10 is capable of continuously monitoring halogen leaks within the enclosure. Further, the current drawn through the heater/anode element 13 of the sensor 12 is applied as an analog signal to a heater current analog-to-digital (A/D) converter 44, which converts this analog signal to a corresponding digital signal to be applied to the microcontroller 62.

In a further aspect of this invention as shown in FIG. 1, an automatic zeroing circuit 78 is provided to initially take a reading of the sensor 12 as would be indicative of a steady state or background level of the halogen in an enclosure to be monitored. The background sensor signal is stored in a non-volatile memory within the circuit 78 and is subtracted, as will be explained later, from the current sensor signal to provide a compensated signal as indicative of an increase of the current halogen level over the original background level thereof. Further, the microcontroller 62 is coupled to a transceiver 60 and adapts the microcontroller 62 for the transmission and reception via a serial communication port 86 of data messages to and from a main controller (not shown). In this fashion, a plurality of the halogen monitoring apparatus 10 may be employed at a plurality of remotely disposed refrigerators to detect halogen gas leakage from their compressors and to report such leakage to the main controller.

Figure 2B:
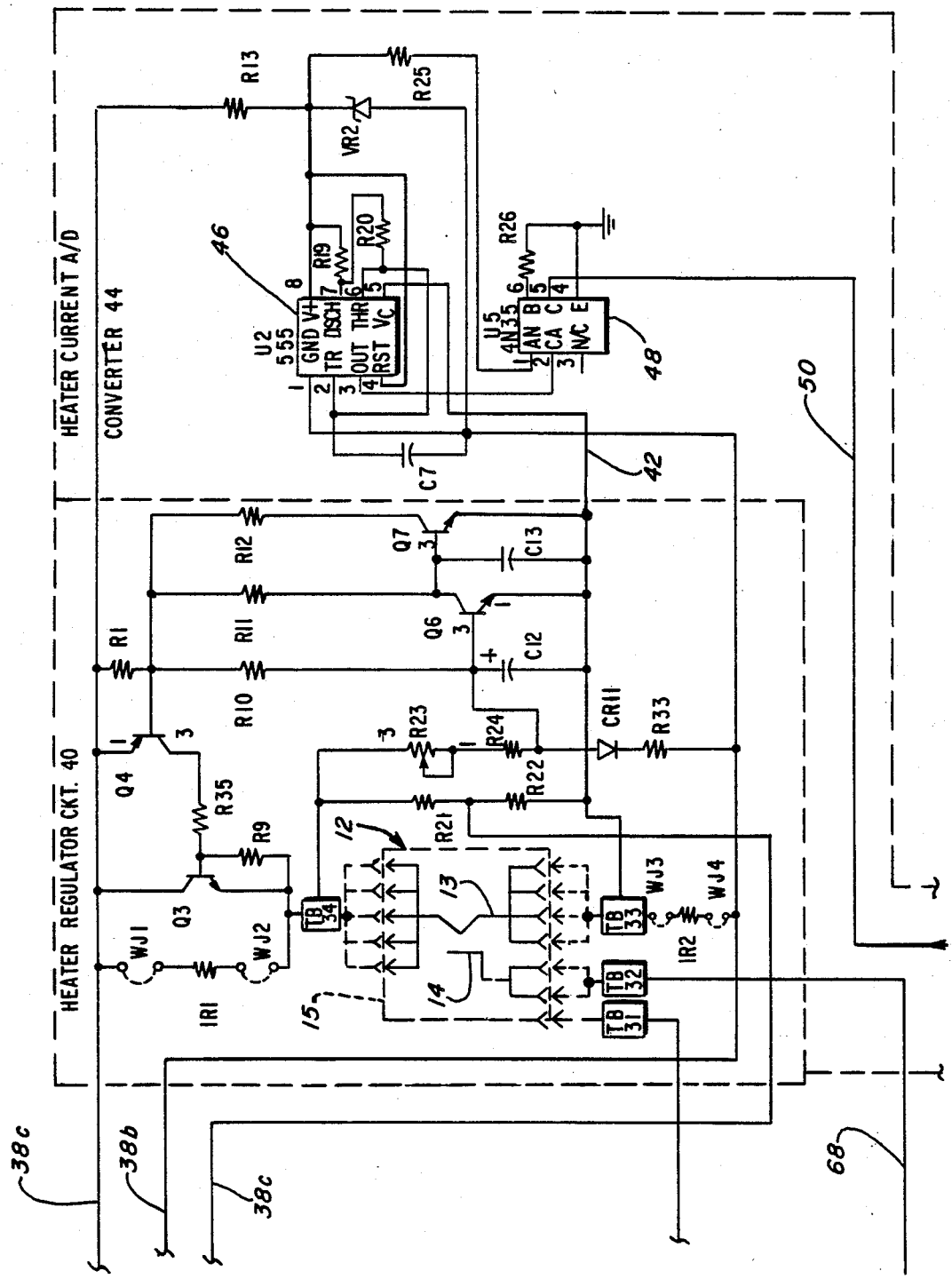

As shown in FIG. 2A, energization in the illustrative form of 120 volts AC is applied to terminals TB 11 and 12 of the surge protection and line filtering circuit 16. The output of circuit 16 is applied to the power supply 20 including a transformer 18. In particular, the output of circuit 16 is applied to a primary winding 18a of the transformer 18, being inductively coupled to each of a plurality of secondary windings 18b, 18c, 18d and 18e. The output of the secondary winding 18b is full wave rectified to provide 10 volts DC to the heater regulator 40 as shown in FIG. 2B, whereby the current passing through the heater/anode element 13 and therefore its temperature may be accurately regulated. See U. S. Pat. No. 3,912,967 of Longenecker. Briefly, the resistance presented by the heater/anode element 13 is sensed and is used to selectively close the transistor Q3 when the resistance of the element 13 is less than a desired value and to open the transistor Q3 when the resistance exceeds this value as would establish the desired temperature of the halogen sensor 12.

Figure 2C:
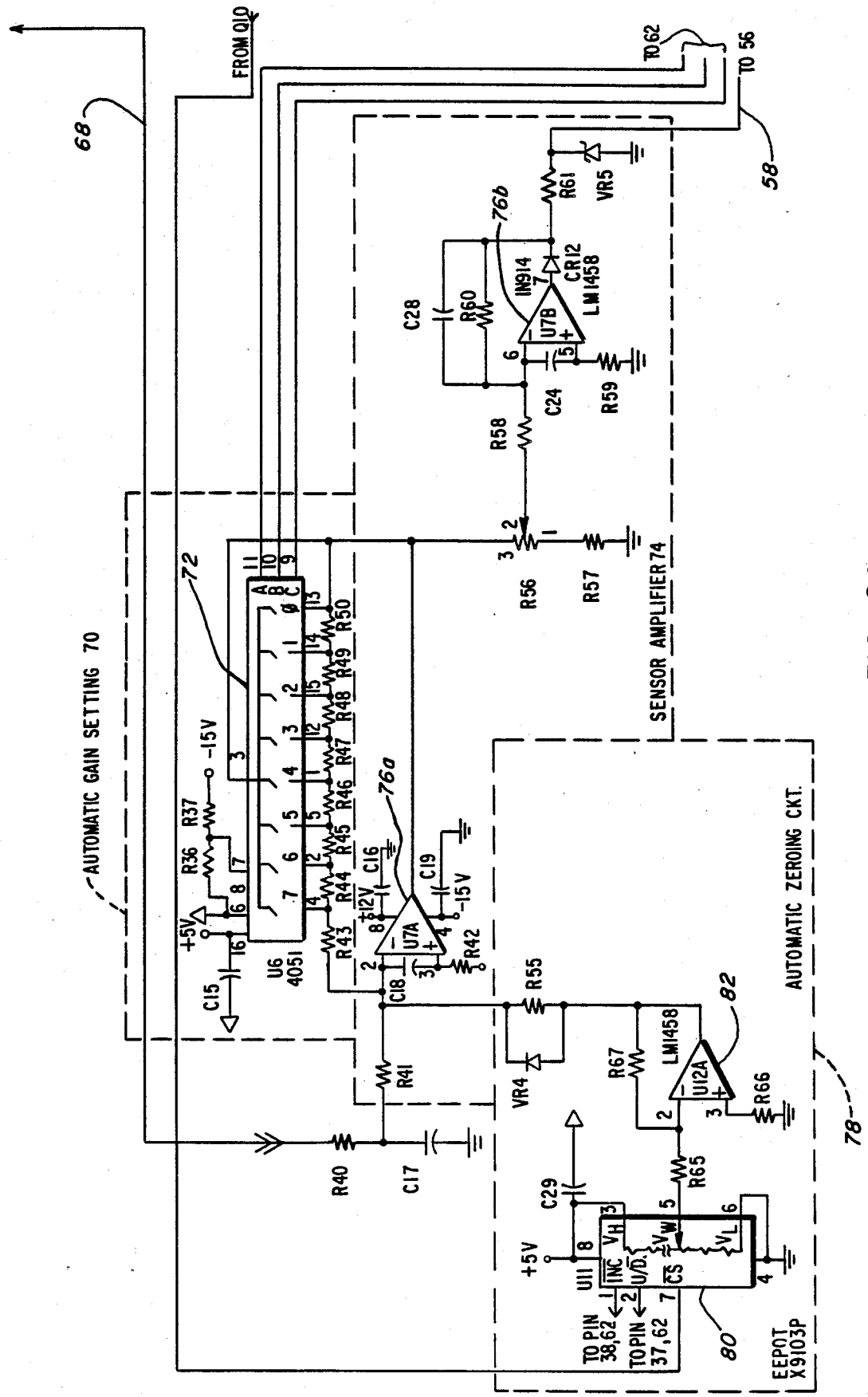
Figure 2D:
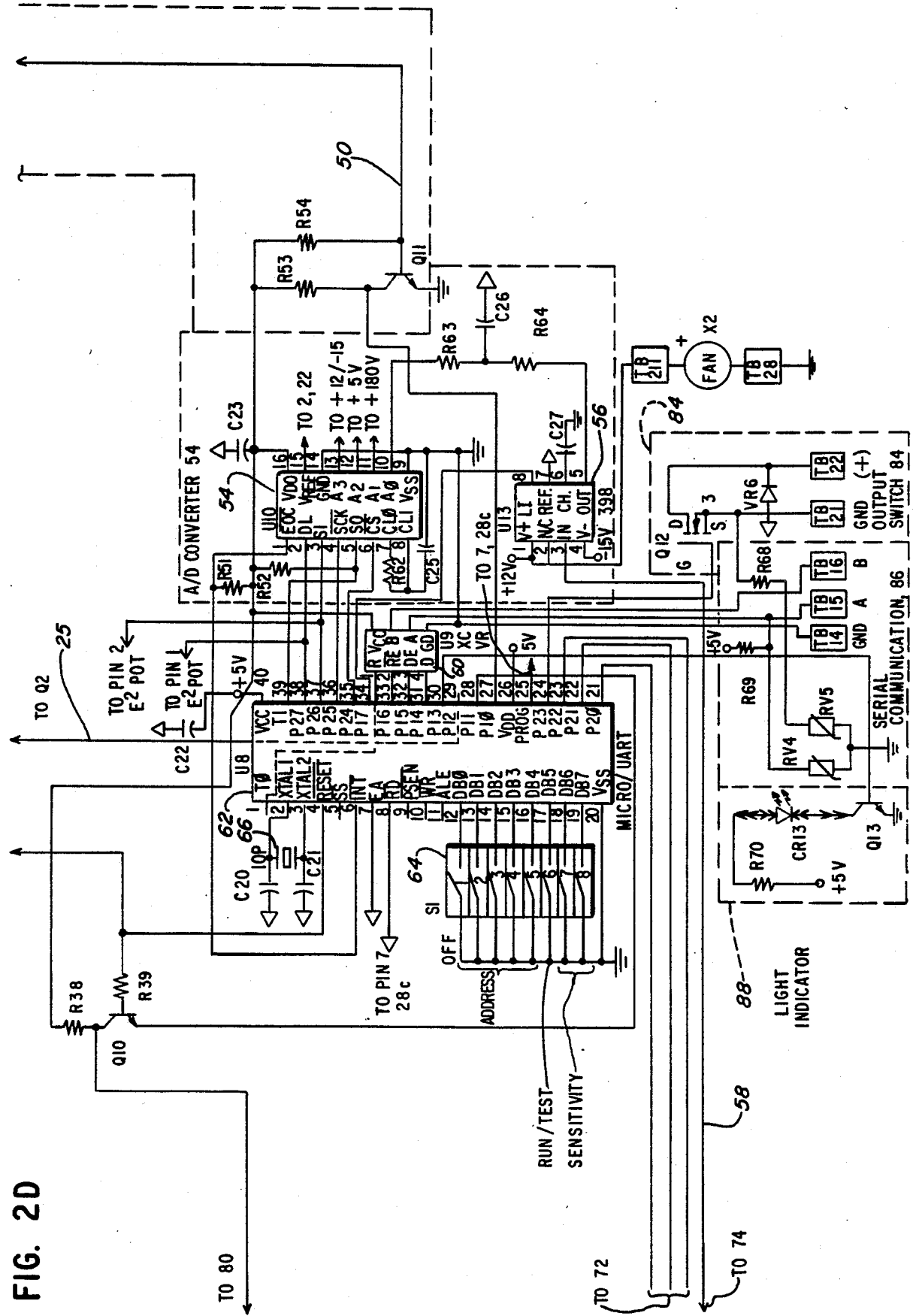

The output of the secondary winding 18c of the power supply 20 is half wave rectified and is applied to the power control switch 24, which controls the application of the relatively high voltage, e.g., 180 volts, between the heater/anode element 13 and the collector/cathode element 14 of the halogen sensor 12 and, in particular, the voltage applied to the point of interconnection of the resistors R21 and R22 of the heater regulator circuit 40. As will be explained, a control signal is developed by the microcontroller 62 as shown in FIG. 2D and applied via control line 25 to a sensor collector/anode over current protection circuit 27, which in turn provides an output to the power control switch 24 and in particular to its transistor Q1, which as will be explained removes (short circuits) the high voltage as applied between the elements 13 and 14 of the halogen sensor 12. Briefly, the microcontroller 62 under the control of its program as shown in FIGS. 3A to 3F, responds to an output on the sensed current line 68 to render the transistor Q1 conductive, whereby the high voltage is removed and the life of the halogen sensor 12 extended.

The voltage appearing on the secondary winding 18d of power supply 20 is applied to a brown-out protection circuit 30, which prohibits the microcontroller 62 from initiating the execution of its program if the 120 volts AC applied to the surge protection and line filtering circuit 16 should decrease as under brown out conditions. Almost immediately after application of 120 volts AC to the surge protection and line filtering circuit 16, a voltage comparator 28a responds to the 2.5 volts on its inverting input pin 8 as derived from the voltage reference circuit 22, whereby the open collector output of the voltage comparator 28a is forced to ground, which is turn forces the $\overline{\text{RESET}}$pin 4 of the microcontroller 62 to reset until the voltage appearing at the point of interconnection between resistors R14 and R15 rises to at least 7.5 volts. At that point, the voltage at the non-inverting input of the voltage comparator 28a exceeds the 2.5 volts at the inverting terminal of the voltage comparator 28a, and the open collector output switches from being grounded to a floating output, which is pulled up to 5 volts via resistor R18, thus forcing the $\overline{\text{RESET}}$pin of the microcontroller 62 high, which hence initiates the microcontroller 62 into executing its instructions.

As shown in FIG. 2A, a RESET circuit 32 is provided to ensure that the microcontroller 62 is initially RESET when power first comes on. As will be explained, a watchdog circuit 34 is provided to prevent the RESET circuit 32 from further preventing the microcontroller 62 from being RESET. The watchdog circuit 34 in the form of a voltage comparator 28c is coupled to pin 8 of the microcontroller 62 to monitor the proper execution of the program by the microcontroller 62. As long as the program continues to be executed properly by the microcontroller 62, its RD pin 8 regularly applies a stroke pulse signal to the noninverting input of the voltage comparator 28c providing 0 output pulses which prevent microcontroller 62 from being RESET. The output of the voltage comparator 28c is in turn coupled to a RESET circuit 32 and in particular to the point of interconnection of a capacitor C14 and a resistor R32 which form a timing circuit 36. The timing circuit 36 has a time constant of 47 msecs., and the voltage across the capacitor C14 is applied to the inverting input of a voltage comparator 28b. A voltage divider comprised of the resistors R29 and R30 applies ½ of the output of the 5 volt regulator Q5 to the non-inverting input of the voltage comparator 28b as a reference level for the reset circuit 32. Approximately 32 msecs. after power is initially applied to the surge protection and line filtering circuit 16, the capacitor C14 is charged to a level exceeding that of the reference voltage divider, whereby the output of the voltage comparator 28b would be forced to ground, and hence cause a reset of the microcontroller 62. After the microcontroller 62 has been initially reset upon power-up and has started to execute its program, the microcontroller 62 outputs the strobe pulse from the $\overline{\text{RD}}$pin 8 indicating that the program is being properly executed by the microcontroller 62. In particular, the strobe pulse regularly discharges the capacitor C14 at least every 32 msecs., thereby preventing the reset circuit 32 from resetting the microcontroller 62 while its program is being properly executed.

As explained above, the output of the halogen sensor 12 is responsive to the ions collected by the collector/cathode element 14 and is applied via the sensed current line 68 to a variable high gain amplifier comprising an automatic gain setting circuit 70 and the sensor amplifier 74. A high gain amplifier is required because the output current of the halogen sensor 12 is relatively small in the order of 1-100 mamps. In particular and referring now to FIG. 2C, the sensor output is applied to an operational amplifier 76a whose output is in turn applied to a second operational amplifier 76b. A feedback circuit as would control the gain of the operational amplifier 76a is formed by the automatic gain setting circuit setting 70, which takes the form of an analog multiplexer 72, using the generic industry standard designation 4051. As will be explained later, the analog multiplexer 72 operates under the control of the microcontroller 62 to short out a selected portion of a voltage divider comprised of resistors R43 to R50 to thereby set the gain of the operational amplifier 76a. By so adjusting the gain of the operational amplifier 76a, various ranges of current levels of the halogen sensor 12 and thereby various ranges of halogen compound densities may be detected and accurately measured. The selectively amplified output of the operational amplifier 76a is applied further to the operational amplifier 76b to provide the output of the sensor amplifier 74 on input line 58. The output from the amplifier circuit 74 corresponds to ranges of halogen leaks of $1\times 10^{-4}$, $1\times 10^{-5}$, $1\times 10^{-6}$, and $1\times 10^{-7}$ cc/sec corresponding respectively to the tap settings 7 and 6, 5 and 4, 3 and 2, and 1 and 0 of the analog multiplexor 72 as selected under the control of the microcontroller 62. In this embodiment, each range corresponds to two tap settings. It is now apparent that the halogen monitoring apparatus 10 differs from the prior art in that continued monitoring by an operator to select the size of the halogen leak to be detected by actuating a mechanical rotary switch to select the various gains of its sensor amplifier circuit is no longer needed in that this apparatus 10 employs an automatic gain setting circuit 70 under the control of the microcontroller 62.

The automatic zeroing circuit 78 is incorporated into the halogen monitoring apparatus 10 to eliminate those steady-state signals from the halogen sensor 12 as may be due to the operation of the sensor 12 itself or to the presence of residual or background amounts of halogen compounds in the enclosure being monitored. In a contemplated application of the halogen monitoring apparatus 10 where it would be used to continuously monitor halogen leaks within an enclosure for relatively prolonged periods of time, the automatic zeroing circuit 78 under the control of the microcontroller 62 measures the level of the background steady-state signal as originate from the halogen sensor 12 and serves to store and continuously subtract that level from the halogen sensor output signal as applied to the sensed current line 68. In particular, the automatic zeroing circuit 78 includes an electrically erasable digitally controlled potentiometer (EEPOT) 80 such as that manufactured by XICOR Inc. under their model number X9103P. The EEPOT 80 comprises a non-volatile memory having an extended memory life, e.g., 100 years, for storing a signal indicative of the position of its wiper arm as corresponds to the initially measured steady-state signal of the halogen sensor 12. That zeroing output is applied via an operational amplifier 82 to be added in series with the halogen sensor output to the noninverting input of the operational amplifier 76a.

Referring now to FIG. 2D, a dipswitch 64 is connected to the inputs DB0 to DB7 of the microcontroller 62 and serves to provide operator input thereto. In particular, a run/test switch 6 of the dipswitch 64 permits the microcontroller 62 to operate in a selected one of a TEST or RUN mode. Initially, the operator sets switch 6 to operate the apparatus 10 in its TEST mode, wherein the halogen monitoring apparatus 10 takes an initial measurement of the background level signal outputted by the halogen sensor 12 and, if the background halogen level is reasonably low (no leak present), the operator changes the position of switch 6 of the dipswitch 64, whereby the microcontroller 62 causes the apparatus 10 to operate in its normal or RUN mode. In the RUN mode, the background signal is stored in the EEPOT 80 and is subtracted from the current output signal of the halogen sensor 12. Thus, the microcontroller 62 will continuously, in its run mode, zero out the current signal from the halogen sensor 12 with the stored background steady-state signal as stored in the EEPOT 80 until recalibration becomes necessary as would occur with the installation of the apparatus 10 and its halogen sensor 12 in a new enclosure or the replacement of the halogen sensor 12.

The analog output of the sensor amplifier 74 is applied via the input line 58 to an IN pin 3 of the sample and hold circuit 56. In turn, the analog output from its OUT pin 5 is applied to an input A0 pin of the A/D converter 54, which converts the inputted analog signal as indicative of the variably amplified halogen sensor output into a corresponding digital signal and applies this digital signal from its output S0 pin 5 to the T1 pin 39 of the microcontroller 62.

The A/D converter 54 is a 4-channel input device and also serves to monitor the power supply levels of the 180 volts, 5 volts and either of the +12 or -15 volts as are outputted from the power supply 20. In a recognized fashion, the microcontroller 62 applies to the $\overline{CS}$ pin 6 of the A/D converter 54 a channel select signal, whereby a selected one of the four input signals as are applied to the A0 to A3 pins is converted to its digital signal and is input to the microcontroller 62.

In normal operation of the halogen sensor 12, the current flowing through its heater/anode element 13 is in the order of 1-4 amps and is picked off from the TB33 terminal and applied to the heater current analog to digital (A/D) converter 44 and, in particular, to its timer 46 as shown in FIG. 2B. The timer 46 operates as a counter to output a signal of a frequency proportional to the current outputted from the heater/anode element 13. The output of the timer 46 is applied via an opto-isolator 48, which serves to protect the microcontroller 62 from the relatively large signals present in the heater regulator circuit 40. The isolator output is applied via output line 50 and a transistor Q11 (see FIG. 2D) to the P10 pin 27 of the microcontroller 62, whereby the heater current and thereby the operation of the halogen sensor 12 maybe monitored.

It is contemplated that a plurality of the halogen monitoring apparatus 10 and their halogen sensors 12 may be disposed at a like plurality of remote stations for monitoring halogen leaks thereat. Each of the halogen monitoring apparatus 10 has the capability of communicating with a centrally disposed main controller in the illustrative form of an IBM-PC/XT ® or compatible microcomputer. The main controller is capable of periodically communicating or polling each of the remotely positioned halogen monitoring apparatus 10. As shown in FIG. 2D, pins P14 to P16 and T0 of the microcontroller 62 are coupled to the transceiver 60 for receiving and transmitting via the port 86 messages to the main controller. The transceiver 60 may illustratively take the form of that chip manufactured by Texas Instruments under the designation 75176 or the equivalent chip made by Fairchild Semiconductor and is capable of transmitting digital data at a baud rate of 1200 bits per second using the format of the "BISYNC" ® protocol. As will be explained in detail below, after a halogen leak has been detected, a status register within the microcontroller 62 is changed to reflect the detected leak. Upon being polled by this main controller, the microcontroller 62 responds by transmitting a "status byte" including various data indicative of the operation of the halogen monitoring apparatus 10, as well as whether a leak has or has not been detected.

Each of the halogen monitoring apparatus 10 is coupled in parallel by a single communication line with the main controller, which poles each of the halogen monitoring apparatus 10 by addressing a particular halogen monitoring apparatus 10 with a unique five bit address, whereby the corresponding microcontroller 62 is enabled to interrogate its memory and to formulate and transmit a return message to the main controller via its transceiver 60. The dipswitch 64 provides a means in the form of its switches 1-5 for entering into the microcontroller 62 its unique address, whereby the main controller may communicate with that particular apparatus 10.

When the microcontroller 62 senses that the halogen sensor 12 has detected a leak as will be explained below, the microcontroller 62 outputs on its P13 pin 30 a signal that actuates a light indicator 88 to flash at an illustrative rate of 1Hz. As was explained above, the halogen sensor 12 is disabled by the microcontroller 62 after sensing a halogen leak. A flashing light indicator 88 indicates that this particular halogen monitoring apparatus 10 and its halogen sensor 12 are in an off state and waiting for a service person to find and correct the leak and to reset the main controller, which will in turn reset the corresponding microcontroller 62. In addition, P23 pin 24 of the microcontroller 62 is coupled to an output switch 84 in the form of a FET Q12, which is operated to turn on when a leak is detected. As indicated in FIG. 2D, the FET Q12 connects terminals TB21 and 22 together, which may be employed to actuate a further alarm manifestation. Upon receiving the return message from the halogen monitoring apparatus 10, the main controller may actuate a beeper to provide a warning manifestation of a detected halogen leak. In addition, the main controller saves all status signals or flags indicative of the detected halogen leak on a suitable memory such as a floppy disk, bubble memory, or EAROM. In turn the main controller may through suitable connections over conventional telephone wires place calls to appropriate management and service personnel to inform them that a leak has been detected.

Figure 3A:
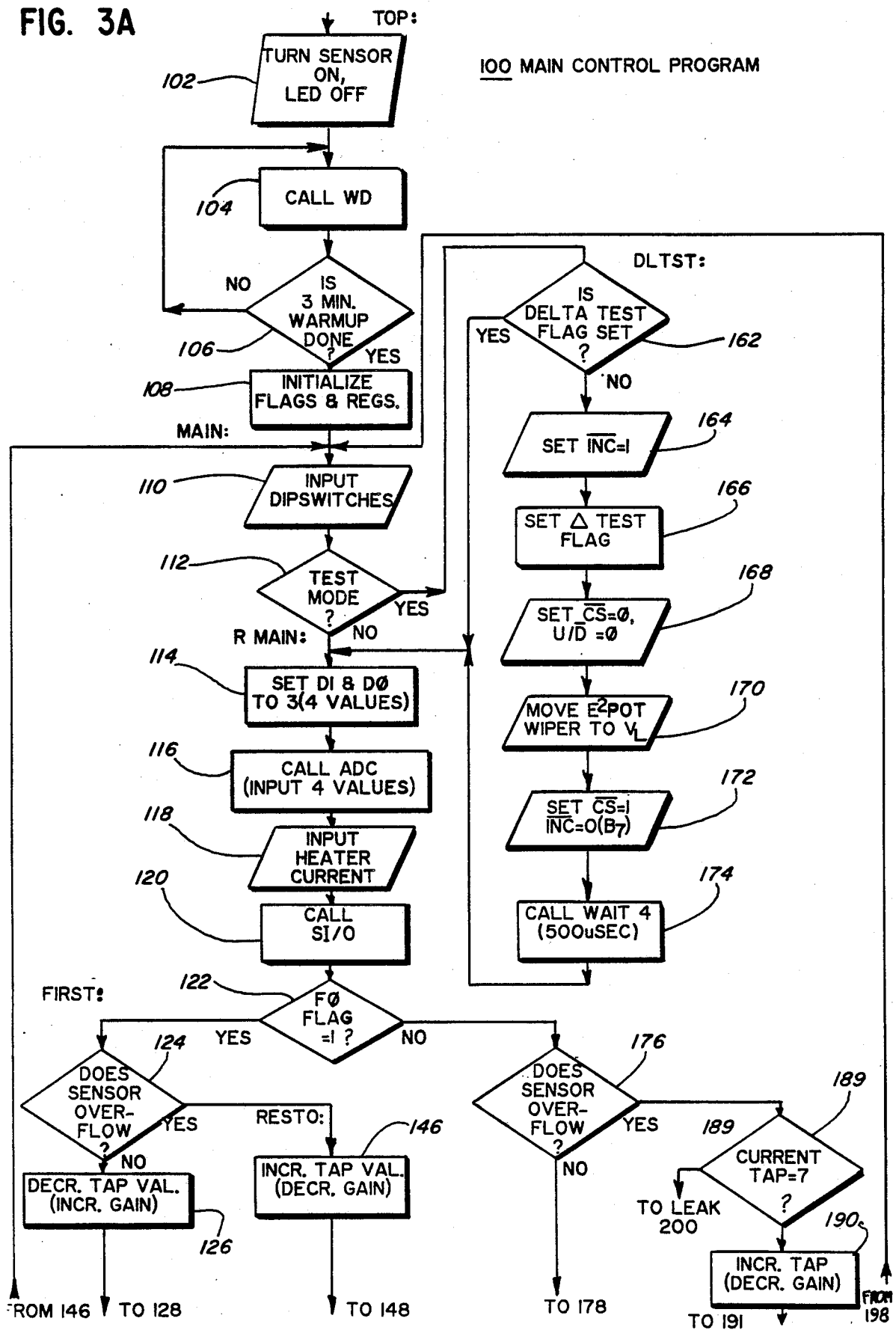
Figure 3A:
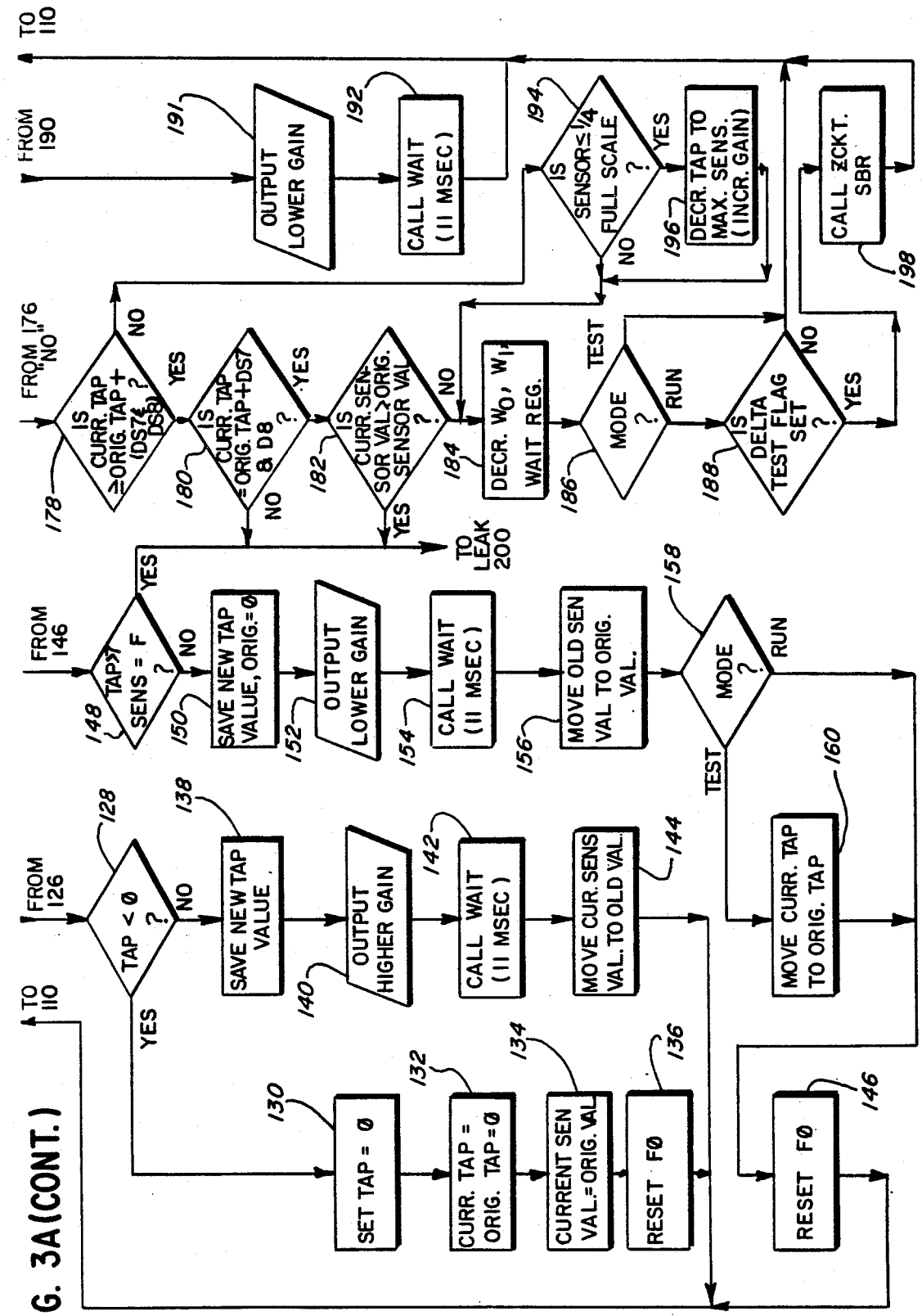

FIG. 3A shows a flow diagram of a main control program 100 as executed by the microcontroller 62 to control the various functions and processes of the halogen monitoring apparatus 10, whereas the remaining FIGS. 3B to 3F show various subroutines 200, 120, 198, 116 and 104 as are selectively called from the main control program 100. Referring now to FIG. 3A, the microcontroller 62 enters the main control program 100 after a high signal has been applied to its $\overline{RESET}$ pin 4 (see FIG. 2D) as is indicative that an input voltage has been applied to the surge protection and line filtering circuit 16 to execute its first instruction 102, whereby the halogen sensor 12 is turned on by setting pin 29 of the microcontroller 62 and the control line 25 to a logic 0, which in turn turns off the transistor Q2 (see FIG. 2A) and thereby the transistor Q1 of the power control switch 24. Thus, the 180 volts derived from the power supply 20 is now applied between the heater/anode element 13 and the cathode/collector element 14 to actuate the halogen sensor 12. In step 102, the light indicator 88 is also turned off, before step 104 effects a 3 minute warmup loop to allow the halogen sensor 12 to stabilize its output current as applied to the sensed current line 68. While in this 3 minute loop, the watchdog subroutine 104, as shown in more detail in FIG. 3F, periodically provides a strobe pulse to the watchdog circuit 34, whereby the timing circuit 36 is defeated as explained above to thereby prevent the resetting of the microcontroller 62. After the 3 minute warmup has been completed as determined in step 106, step 108 accesses the random access memory (RAM) of the microcontroller 62 to initialize the various flags to be used in the course of the main control program 100. In particular, step 108 sets a flag zero (F0) flag to 1 in preparation for further steps in the program 100 and also sets the tap or gain setting of the analog multiplexer 72 to its minimum gain setting, i.e., tap 7. Each time that the halogen monitoring apparatus 10 and its microcontroller 62 is powered up, control will enter the main control program 100 at step 102 and the program 100 will be reinitialized in step 108. Thus each time that the program is powered up, the analog mutliplexer 72 will be set to its minimum gain, so that as will be explained later, the tap setting of the analog multiplexer 72 may be incremented until a predetermined output is obtained from the sensor amplifier 74.

Next, step 110 accesses the inputs from the dipswitch 64 to read into the microcontroller 62 its unique address as set by the switches S1-S5, to determine whether the halogen monitoring apparatus 10 is set in its RUN or TEST mode as by switch S6, and to determine the sensitivity of the halogen sensor 12 as set by switches S7 and S8. As will be explained below, the halogen monitoring apparatus 10 is capable of adjusting its sensitivity to sense only changes of a certain magnitude in the increase of the current level from the halogen sensor 12 as a valid indication of a halogen leak. The use of two switches S7 and S8 permits the setting of four different levels of sensitivity or magnitudes of change of the halogen sensor output.

If step 112 determines that the halogen monitoring apparatus 10 is in its TEST mode as would normally occur at the installation of the apparatus 10 or recalibration of its halogen sensor 12, the program 100 moves to the sequence of steps 162 to 174, which sets the delta flag to 1. The delta flag is set, as will be explained below in detail, in order to enable the calling of the zeroing circuit subroutine 198, whereby the automatic zeroing circuit 78 and, in particular, its EEPOT 80 may be initialized, i.e. the background level of the residual or steady state halogen as sensed by the halogen sensor 12 is stored therein. The delta test flag is used by the main control program 100 to insure that when the run/test switch 6 of the dipswitch 64 has been changed from the test position to its run position and the program 100 is operating therein, the zeroing circuit subroutine 198 will be called only a single time in order to initialize the EEPOT 80. In step 162, the delta test flag is tested to indicate whether it had been previously set as would have occurred by a previous execution of step 166. If the delta test flag has been set to 1, the program 100 returns to step 114; if not set as would occur if the apparatus 10 is in its TEST mode and this is the first execution of the main control program 100, then step 166 sets the delta flag to 1 and step 168 applies a 0 state signal to the pins 1 and 2 of the EEPOT 80. Next, step 170 moves the output wiper arm Vw pin 5 of the EEPOT 80 to its minimum position VL in preparation for the zeroing circuit subroutine 198. Thereafter, the main control program 100 returns to step 114 and the steps 162 to 174 will not be re-executed in that the delta flag is now set to 1.

Next, step 114 sets the channel select registers D1 and D0 within the A/D converter 54 to convert all of its four input channels and an analog to digital (A/D) subroutine 116 is called to convert the following analog input signals into corresponding digital signals: 1) the amplified sensor signal as input to the AO pin 10; 2) a scaled portion of the 180 volt power supply signal as input to A1 pin 11 from the point of interconnection of resistors R5 and R34; 3) a scaled portion of the 5 volt power signal as applied to the A2 pin 12 from point of interconnection of the resistors R16 and R17 of the power supply 20; and 4) the rectified +12 or −15 volt signals as applied to the A3 pin 13 from the point of interconnection of the elements CR10 and VR3. Next in step 118, the pulses outputted by the heater current A/D converter are applied to P10 pin 27 of the microcontroller 62 to be counted. The frequency of these pulses is proportional to the magnitude of the current flowing through the heater/anode element 13. Next, the serial input/output (I/O) subroutine 120, as will be explained in greater detail in FIG. 3C, is called if the main controller wants to receive or to modify the status registers as stored in the RAM of the microcontroller 62.

Next in step 122, the flag zero (F0) flag is tested to see if the sensor amplifier 74 and the automatic gain setting circuit 70 have been initialized. If the F0 flag is still set (F0 flag=1) indicating that the gain tap of the analog multiplexer 72 has not been initialized after the most recent energization of the power supply 20, the main control program 100 moves to step 124. In step 108 as previously executed, tap 7 of the analog multiplexer 72 was initialized, i.e., is set so that the gain of the operational amplifier 76a is initially set at a minimum value. Now, step 124 examines the output of the A/D converter 54 to determine whether it has overflowed, i.e., is greater than a 2.5 volts maximum input level. In many situations, where the enclosure to be tested is substantially free of halogen gas, the main control program 100 will proceed to increase by one tap setting the gain of the analog mutliplexer 72 each time that the step 126 is executed, from its minimum tap 7 until its 0 tap as indicative of the maximum gain, is set. Step 124 continues to test whether the A/D converter 54 was overflowed and, if not, step 126 will increment the gain of the voltage comparator 76a by decreasing the tap setting, e.g. move the analog multiplexer 72 to its next lower tap number. Thereafter, step 128 will determine whether the analog multiplexer 72 is set at its maximum gain, i.e. its 0 tap, and, if not, step 138 stores an indication of the new tap value, e.g. tap 6, into a designated location within the RAM of the microcontroller 62. Next, step 140 switches the setting of the analog multiplexer 72 to the new higher tap setting. Step 142 initiates a wait period of 11 msec until the new tap output has been settled, before step 144 takes a "current" value of the output of the halogen sensor 12 and stores it into a storage location of the microcontroller RAM known as "old value", before the program returns to step 110.

In this fashion, the control program 100 loops repeatedly through step 126 until either the A/D converter 54 overflows as tested in step 124, or the analog multiplexer 72 is set at its minimum tap 0 corresponding to its maximum gain as decided in step 128. In that case, step 130 actuates the analog multiplexer 72 to set its 0 tap for a maximum gain or maximum sensitivity of the halogen monitoring apparatus 10. Next, step 132 stores the indication that the analog multiplexer 72 is in its 0 tap into the "original tap" location of the microcontroller RAM. Next, the "current" value or output of the halogen sensor 12, which was read into the A/D converter 54 previously in step 116, is now set into the "original" value register of the microcontroller RAM, before step 136 resets the F0 flag to 0, indicating that the analog multiplexer 72 has now been initialized. Thus, each time that the main control program 100 is powered up and step 108 initializes the flags and, in particular, sets the F0 flag to 1 and disposes the tap gain of the analog multiplexer 72 to its minimum gain value or tap value 7, the program 100 will normally loop through step 126, whereby the tap of the analog multiplexer 72 will be set incrementally to its minimum position 0 for the maximum gain of the sensor amplifier 74. After the tap setting has been so initialized, step 136 resets the F0 flag to 0. After the analog multiplexer 72 has been so initialized and the F0 flag reset to 0, the main control program 100 will not again enter step 124, but will rather be directed to step 176 as will be explained.

If the F0 flag has not been reset and there is initially some level of halogen concentration within the enclosure, the tap of the analog multiplexer 72 will not be reset to 0, but will be set to a particular tap setting 1 to 7 that will cause the A/D converter 54 to overflow as sensed in step 124. If the A/D converter 54 does overflow, the main control program 100 moves to step 146, which increments the tap setting by one to decrease the gain from that gain setting that caused the A/D converter 54 to overload. If the tap setting of the analog multiplexer 72 is at its minimum setting of 7 and the A/D converter 54 is overflowed as determined in step 148, this is an indication of a leak, in that the concentration of halogen exceeds the minimum sensitivity of the apparatus 10 and the main control program 100 moves to the leak control portion 200 of the program, as will be explained with respect to FIG. 3B. However, if the tap setting is less than 7, step 150 will set this tap setting into the "current" value location of the microcontroller RAM and will also set the "original" value of the tap setting to 0. As will be apparent from the further explanation of the main control program 100, "current" and "original" values of each of the tap settings of the analog multiplexer 72 as well as the "current" and "original" values of the halogen sensor output are saved in corresponding locations within the RAM of the microcontroller 62 to permit determination of increases of the halogen compound concentration levels as will be indicative of a halogen leak. Next, step 152 effects a change of the tap setting of the analog multiplexer 72 to its next lower gain setting, before step 154 effects a delay or wait period until the setting change can be completed. Next, step 156 loads the "old value" of the sensor output into the "original" value location of the microcontroller RAM, before step 158 determines whether the apparatus 10 is operating in its TEST or RUN mode. If in its TEST mode, the "current" value of the tap in step 160 is moved to its "original" value. Thus, if the apparatus 10 is operating in its TEST mode, the tap setting obtained in step 150, as would be indicative of the quantitative or non-zeroed background level of halogen gas, is saved in the "original" value location of the microcontroller's RAM, whereby the "original" value of the tap setting as taken in the zeroing circuit subroutine 198 and stored in the EEPOT 80, as will be explained, will be ignored to obtain a relative leak detection with regard to present levels of halogen. If in the RUN mode, the main control program 100 moves directly to step 146 which resets the F0 flag indicating that the analog multiplexer 72 has been initialized. Thus if the program is in the RUN mode as would normally occur, the "original" value of the tap setting as would normally be 0, corresponding to a maximum gain of the sensor amplifier 74, will be set in the "original" value of the microcontroller's RAM, whereby in the further running of the main control program 100, current readings of the sensor output would be compensated with respect to the initially taken background level of the sensor output.

In the next loop of the main control program 100 after the F0 flag has been reset to 0 in either of steps 136 or 146, step 122 will direct the program 100 to step 176, which determines whether the output of the A/D converter 54 has overflowed. If in the overflow state, step 189 determines whether the tap setting of the analog multiplexer 72 is at its maximum tap setting of 7 and, if so, the main control program 100 provides an indication of a leak and the program 100 moves to leak control at 200, as will be explained. If not at tap setting 7, step 190 increments the tap by one position and decreases accordingly the gain of the sensor amplifier 74. Step 191 effects a change of the tap to its next higher setting, and step 192 effects a delay to permit the setting to be completed, before the program 100 returns to step 110.

On the other hand, if the A/D converter 54 has not overflowed after the F0 flag has been reset, the main control program 100 now determines whether there has been a halogen leak as by comparing variously the change of the "current" values and "original" values of the tap settings of the analog multiplexer 72 and the output signals of the halogen sensor 12. In a significant aspect of this invention, the halogen monitoring apparatus 10 is capable of selecting different sensitivities to halogen compounds in the enclosure, i.e. smaller or larger changes of halogen compound concentrations with a particular enclosure may be selectively set for the apparatus 10 to provide an indication of a halogen leak. To this end, sensitivity switches 7 and 8 of the dip switch 64 may be variously set in any of four different combinations that corresponds to a change or "adder" from the original analog multiplexer 72 tap position by 1, 3, 5 or 7 tap positions.

First, in step 178, the "current" tap position is compared to the "original" value thereof plus the above sensitivity "adder" as entered by the dip switch 64 and, if greater or equal to the original tap position plus the sensitivity "adder", then step 180 determines whether the "current" value is not equal to the original value of the tap setting plus the sensitivity "adder", as would indicate that the "current" value of the tap setting is greater. If greater, the main control program 100 provides an indication of a leak and moves to the leak control at location 200. On the other hand, if the "current" value of the tap setting is equal to the original value of the tap setting plus the sensitivity adder, step 182 performs a further test of whether the "current" value of the halogen sensor output is greater than the "original" value of the halogen sensor output and, if so, the main control program 100 provides an indication of a leak and also moves to the leak control location 200.

Returning again to step 178, if the "current" value is not greater than the "original" value of the tap setting plus the sensitivity "adder", the main control program 100 moves to step 194 to determine whether the output of the A/D converter 54 is less than ¼ full scale thereof and, if not or greater, the "current" value within the "wait registers" W0 and W1 is decremented in step 184 by 1 to a minimum of 0. The "wait registers" are used to indicate that a leak indication has occurred and that a wait period has expired, noting that the halogen monitoring apparatus 10 requires that three successive halogen leak indications and wait periods occur before a valid halogen leak and a warning signal thereof is provided. On the other hand, if the output of the A/D converter 54 is less than ¼ full scale, step 196 decrements the gain by one tap to give sensor amplifier 74 maximum sensitivity, before returning to step 184. Next, step 186 tests the dip switch 64 to determine whether the main control program 100 is operating in its RUN mode and, if still in its TEST mode, the main control program 100 returns to its step 110. On the other hand if in its run mode, step 188 tests whether the delta test flag is set to 1 as would indicate that the operator has just set the run/test switch 6 of the dipswitch 64 from TEST mode to its RUN mode and, if set, the zeroing circuit subroutine 198, as will be further described with respect to FIG. 3D, is called. As will be explained later, the zeroing circuit subroutine 198 causes the EEPOT 80 to output the initial steady state signal, which cancels out the background level of halogens within the enclosure and stores a signal indicative of the position of its wiper arm in a non-volatile memory. That stored value of the wiper arm will be applied to the inverting input of the operational amplifier 82, which inverts and multiplies by 2 the voltage from the EEPOT 80 and applies that signal to the inverting input of the voltage comparator 76a. As will be explained, the zeroing circuit subroutine 198 will reset the delta test flag to 0, whereby the background level of the halogen sensor 12 will be calculated only at installation time, initially stored into the non-volatile memory of the EEPOT 80 and will not be reset until the halogen sensor 12 is replaced and/or the halogen monitoring apparatus 10 is again recalibrated by the operator.

Thus, it is seen that the main control program 100 and in particular its steps 176 to 196 serve to provide an indication of a halogen leak under the following conditions:

(1) when the "current" value of the tap position of the analog multiplexer 72 is greater than the "original" value of the tap position plus the sensitivity adder as entered on switches 7 and 8 the dip switch 64;

(2) when the "current" value of the tap position is equal to the "original" value of the tap position plus the sensitivity adder and the "current" value of the halogen sensor output exceeds its "original" value; and (3) when the output of the A/D converter 54 overflows and the gain tap of the analog multiplexer 72 is set at its minimum gain position 7.

Referring now to FIG. 3B, leak control location 200 is shown in detail. Location 200 is entered when a predetermined change in the output of the halogen sensor 12 has been detected in accordance with that criteria as explained above. The leak control location 200 verifies whether such a change as may be indicative (or not) of a leak are valid or spurious. In a significant aspect of this invention, when a leak change is so provided, step 202 removes the 180 volts as applied between the collector/cathode element 14 and the heater/anode element 13 of the halogen sensor 12 by setting the P12 pin 29 of the microcontroller 62 to a logic high as applied by the control line 25 to turn on transistor Q2, the isolator 26 and thus the transistor Q1, whereby the 180 volts as applied across the output of the secondary coil 18c is shorted out and the halogen sensor 12 is essentially deenergized. As a result, the collector/cathode element 14 no longer collects its current as would otherwise significantly shorten the life of the halogen sensor 12. Next, step 204 reads the dip switch 64 to determine which position switch 6 of the dipswitch 64 is in and thus whether the halogen monitoring apparatus 10 is in its TEST or RUN mode. If in the RUN mode, the program moves to step 206, which increments by one a counter formed by the W0 and W1 wait registers within the microcontroller RAM. Each time that a leak is confirmed at location 200 when in the RUN mode, this wait counter will be incremented by 1. Next, step 208 tests whether the wait counter has been incremented three times as would qualify for a verified leak as opposed to a nuisance or spurious indication. If the wait counter has not been incremented to three, the program moves to step 210 to set the leak wait mode flag, as will now be available to be transmitted to the main controller informing it that the halogen monitoring apparatus 10 is in the process of testing whether a valid halogen leak has occurred. At this point in time, a five minute timing period occurs. Initially, in step 212, a three minute waiting period is commenced during which the serial I/O subroutine 120 is called in order to permit communication between this halogen monitoring apparatus 10 and the centrally disposed main controller, and the watchdog subroutine 104 as shown in FIG. 3F is called to continuously reset or refresh the watchdog circuit 34, whereby the microcontroller 62 will not be reset. At the end of this three minute period, step 214 turns off the transistor Q1 by permitting the P12 pin 29 of the microcontroller 62 to go high, whereby the halogen sensor 12 is turned back on for a two minute warm up period to permit its operation to settle before taking the next A/D sample of the halogen sensor 12. Further, step 216 calls the serial I/O subroutine 120 and the watchdog subroutine 104. After the two minute warm up period, step 218 resets the leak wait mode flag indicating that the waiting period is over and the program returns to step 110 of the main control program 100.

If step 208 tests the wait counter registers W0 and W1 and determines that three leak detections and corresponding wait period have occurred, there is a valid indication of a halogen leak within the enclosure and the program moves to step 220, which clears the wait counter registers W0 and W1 to zero. After step 220, or if step 204 determines that the halogen monitoring apparatus 10 is operative in its TEST mode, the program goes to step 222, which sets the tap of the analog multiplexer 72 to its minimum gain setting 7, before step 224 sets the tap setting to 7. Next, step 226 resets the leak wait mode flag indicating that the halogen monitoring apparatus 10 has not detected a halogen leak and is processing the three wait periods. Next, step 228 sets a leak detect flag indicating that a leak has been detected and has been validated as decided in step 208 and further activates the FET Q12 by placing a logic one on P23 pin 24 of the microcontroller 62 to enable an external alarm as indicative of a valid leak. The leak control subroutine 200 now enters a loop through the steps 230 to 236. Step 230 energizes the light indicator 88 to flash to provide a visual indication that a validated halogen leak has been determined, before the serial I/O subroutine 120 is called to permit communication between the remote halogen monitoring apparatus 10 and the centrally disposed main controller. The watchdog subroutine 104 is called to periodically strobe the watchdog circuit 34 thereby preventing the resetting of the microcontroller 62. Next, step 236 determines whether the leak detect flag has been set or reset. If set, the program will continue to loop through steps 230 to 236, until the halogen leak within the enclosure has been monitored and cleaned up, and the main controller has transmitted a command to this apparatus 10 resetting its leak detect flag. After being reset, step 236 returns the program to step 102.

Referring now to FIG. 3C, the details of the serial I/O subroutine 120 will be explained. The microcontroller 62 executes the serial I/O subroutine 120 to operate its transceiver 60 in either its transmit or receive modes to respectively transmit messages via its serial communication port 86 to the centrally disposed main controller or to receive messages therefrom. Referring to FIG. 2D, the microcontroller 62 actuates its enable line pin 32 to a logic one to transmit a message via its transmitter pin 31 and, conversely, enables its enable line pin 33 to a logic zero to receive messages from the transceiver 60 via its receiver line pin 1. In this fashion, each of the plurality, e.g., 32, of halogen monitoring apparatus 10 is capable of communicating with its centrally disposed main controller over a common transmission line in a polling scheme, which requires that each of the apparatus 10 has its own unique address as set by switches 1 to 5 of its dipswitch 64. Thus, if the main controller wants to receive or transmit a message to a particular apparatus 10, the main controller must utilize a predetermined protocol, e.g., BISYNC®, and include in the message the address of the particular apparatus 10 it wishes to poll.

Referring to FIG. 3C, when the serial I/O subroutine 120 is called, step 302 disables the transmitter of the transceiver 60 by setting pin 32 of the microcontroller 62 to a logic low, and enables the receiver of the transceiver 60 by setting its pin 33 also to a logic low. Next, step 304 tests pin 1 of the microcontroller 62 for any change applied thereto from the main controller through the serial communication port 86 and the transceiver 60 within a 100 msec. period, and if no activity is present on this receiver line, the serial I/O subroutine 120 is exited, after step 322 tests to determine if the main controller had previously sent t this halogen monitoring apparatus 10 a disable command, i.e., the disable flag has been set. Such disable commands permit the main controller to selectively disable selected of the apparatus 10. If this apparatus 10 is disabled, the serial I/O subroutine 120 returns to step 302 and will continue in this loop until the main controller transmits a message to this apparatus 10 to RESET its disable flag.

On the other hand, if a signal has been applied to the serial input pin 1 of the microcontroller 62 as determined by step 304, the subroutine 120 moves to step 306 which synchronizes the microcontroller 62 with the 1200 baud data message being transmitted by the main controller. Next, step 308 inputs the transmitted message to the microcontroller 62 from the main controller; the transmitted message comprises an OP-ADDR byte, which includes a read or write command plus the address of the polled apparatus 10, and a status byte which may command the addressed halogen monitoring apparatus 10 to reset or disable itself. In step 309, the ACK-/NAK flag is tested, which can only be set below in step 318 after the apparatus 10 has finished transmitting to the main controller. If the ACK/NAK flag is set, then the flag is reset at step 311, the subroutine is exited at step 313, and the program resumes to the next instruction after the call to Serial I/O subroutine 120. If the ACK/NAK flag is not set, Step 310 determines whether the address sent by the main controller matches that of this apparatus 10 as set by its dipswitch 64. If the transmitted and retained addresses are different or if there are errors in the message received from the main controller, the subroutine 120 returns to step 322. If the addresses match, i.e., the main control is transmitting its message to this apparatus 10, then step 310 disables the receiver of the transceiver 60 by applying a logic one output to the $\overline{RE}$ pin 2 of the transceiver 60 and enabling the transmitter of the transceiver 60 by applying a logic one output to the DE pin 32 of the transceiver 60. Next, step 314 reads the status byte as presently transmitted from the main controller. If the main controller has commanded this apparatus 10 to operate into its READ state, its status registers as formed in the RAM of the microcontroller 62 are accessed and a message is transmitted in step 316 via its pin 31 to the main controller in the correct BISYNC® format. The message includes the following data: (1) the positions of the switches 6 to 8 of the dipswitch 64 as would be indicative of the desired sensitivity and whether this regulating circuit 10 is in its RUN or TEST mode; (2) the status flags-leak wait mode, leak detect mode, disable mode; (3) the "original" and "current" values of the tap positions of the analog multiplexer 72; (4) the "current" value of the output signal of the halogen sensor 12; (5) the "original" value of the output of the halogen sensor 12; (6) the value of the 180 V; (7) the value of the 5 V; (8) the value of the $+12/-15$ V; and (9) the value of the heater current.

An important note to realize here is that the current values of tap position and sensor magnitude are transmitted frequently to the main controller. When the predetermined level of halogen gas has been exceeded, the quantitative value can be computed and displayed by the main controller, whereby the urgency of the leak detect flag signal can be evaluated by the service operator.

Next, step 318 sets the host ACK/NAK flag to tell the halogen monitoring apparatus 10 that the next incoming message from the main controller is an acknowledged signal indicating that the main controller received the message transmitted from the apparatus 10 in step 316 or a negative acknowledge signal indicating that it did not. Step 320 then disables the transmitter of the transceiver 60 and the receiver thereof is enabled, before the subroutine 120 returns to step 308 to wait for the ACK/NAK message from the main controller.

If step 314 has examined the status byte from the main controller and determines that it directs the apparatus 10 to operate in its WRITE state, the subroutine 120 moves to step 322, which causes an acknowledge message to be transmitted back to the main controller with the same OP/ADDR field that the main controller had sent to this apparatus 10. After such a transmission, step 324 then disables the transmitter and enables the receiver of the transceiver 60 to receive the next transmission of the main controller. Next, step 326 reads the status byte to determine if the main controller has sent a reset command to set the reset mode flag; if the reset mode flag has been set, step 338 resets the leak wait mode and the leak detect flags before exiting this subroutine 120 and returning to the calling step. On the other hand, if there is no reset command as determined by step 326, step 328 determines whether a disable command has been sent from the main controller and, if true, step 330 sets the disable flag. Thereafter, step 336 effects a return to the calling step. If the disable flag is not set, then step 334 resets the disable flag and the subroutine 120 is exited in step 336.

Referring now to FIG. 3D, the detailed steps of the zeroing circuit subroutine 198 are shown. As described above with regard to the main control program 100, the zeroing circuit subroutine 198 is called if steps 186 and 188 determine that the operator has just changed the run/test switch 6 of the dip switch 64 from the TEST mode to the RUN mode. In that case, the zeroing circuit subroutine 198 is called to cancel out the steady state background level signal outputted by the halogen sensor 12, and to remember (store) that signal level permanently until it is reprogrammed when this halogen monitoring apparatus 10 would be reinstalled in a new enclosure, the halogen sensor 12 is replaced or the apparatus 10 is otherwise recalibrated. Initially in step 400, the delta test flag is reset, so that the zeroing circuit subroutine 198 is called just once between recalibrations of the halogen sensor 12. Next, step 402 sets a counter of the EEPOT 80 to a predetermined count, e.g. 99, to keep track of the 99 positions of the output wiper arm on the VW pin 5 of the EEPOT 80. Next, step 404 tests whether this wiper arm is not at the maximum voltage position VH and, if not, step 406 actuates the indicated inputs of the EEPOT 80, before step 408 commands and step 412 moves the wiper arm up one position to raise the output voltage by 0.05 V at the inverting input of the operational amplifier 82, which multiplies that increase by minus 2 to place an additional $-0.1$ V at the inverting terminal of the operational amplifier 76a. The output of the halogen sensor 12 is converted in subroutine 116 to a digital signal, which is also applied to the input of the operational amplifier 76a. Next, step 424 examines pin 10 of the A/D converter 54 to determine whether the output of the halogen sensor 12 is still greater than or equal to ½ of its full scale value. If so control of the zero subroutine 198 returns to step 404 and the zeroing circuit subroutine 198 will stay in the loop of steps 404 to 424 until the output of the A/D converter 54 falls below ½ full scale.

When less than ½ full scale, the subroutine 198 moves to step 426 to test the gain tap of the analog multiplier 72 and, if not set to its maximum gain tap, i.e. its zero tap, then step 428 decreases the tap gain and step 430 physically changes the tap to the next lower setting to increase the gain of the operational amplifier 76a. The subroutine 198 will loop through steps 426 to 438, until the A/D converter 54 overflows in response to the output of the halogen sensor 12. When overflow does occur as sensed by step 438, control of the subroutine 198 returns to step 404 and the position of the wiper arm of the EEPOT 80 is once again incremented as in step 408 until the output from the A/D converter 54 of the halogen sensor 12 falls below ½ full scale.

When either the wiper arm of the EEPOT 80 reaches its maximum setting VH as determined by step 404 or the gain tap of the analog multiplexer 72 reaches its maximum gain setting of zero as determined by step 426, the zeroing circuit subroutine 198 moves to step 440. Step 440 tests the input pin 10 of the A/D converter 54 for an input of the halogen sensor 12 for overflow. If there is an overflow, step 442 increments the tap of the analog multiplexer 72 to thereby decrease the gain of the sensor amplifier 74. Next step 444 tests whether the gain tap of the analog multiplexer 72 is at its minimum gain position 7. If at its minimum gain position and, as tested in step 440, the A/D converter output overflows, there is an indication of a leak detection and the program control jumps to step 200 to process a leak being detected. If the gain tap of the analog multiplexer 72 is not at its minimum position 7, step 446 further increments the tap position of the analog multiplexer 72 to decrease the gain of the sensor amplifier 74 and the subroutine 198 continues to loop through step 440, until the A/D converter output does not overflow as determined by step 440. In particular, step 446 effects a change of the tap to the next highest setting to thereby decrease the gain of the sensor amplifier 74. Thus, the zeroing circuit subroutine 198 adjusts the position of the output of the EEPOT 80 from its minimum value VL to that value at which a compensating voltage as output by the operational amplifier 82 will cancel or substantially cancel the background signal as derived from the halogen sensor 12. The compensating output of the operational amplifier 82 is applied to the inverting input of the operational amplifier 76a, whereby its output is substantially zero. At that point, the position of the wiper arm of the EEPOT 80 is set in a mechanical sense and a signal indicative of its position stored in its non-volatile memory in the form of the counter. Thus, until the halogen monitoring apparatus 10 is recalibrated, the EEPOT 80 will output a signal corresponding to the background level of halogen as provided by the halogen sensor 12 when the zeroing circuit subroutine 198 was executed initially in response to the run/test switch 6 being disposed from its test to run positions. The setting of the wiper arm of the EEPOT 80 will not be changed until the halogen sensor 12 is recalibrated and the run/test switch 6 is again reset from its test to run positions.

When overflow does not occur as tested in step 440 the subroutine 198 moves to step 454, wherein the tap setting of the analog multiplexer 72 is set to the "original" value thereof as stored in the microcontroller's RAM and step 456 saves the output of the sensor amplifier 74 as derived from the halogen sensor 12 into the "original" value location of the microcontroller's RAM. Thereafter, the subroutine 198 exits and returns to step 110 of the main control program 100.

Referring now to FIG. 3E, the detailed steps of the analog to digital (A/D) subroutine 116 will now be explained. The A/D subroutine 116 converts any of the analog signals as applied to the A/D converter 54 including the amplified sensor signal from the halogen sensor 12, a scaled down 180 volt power supply signal, a scaled down 5 V power supply signal, and either of the rectified +12 or −15 power supply voltages, as respectively applied to the pins 10 to 13 of the A/D converter 54. When the A/D subroutine 116 is called from any of a number of points in the program, control jumps to step 500, which causes a message indicative of the selected channel(s) to be sent serially from pin 37 of the microcontroller 62 to pin 3 of the A/D converter 54, where it is stored in a pair of registers D0 and D1. If the selected input signal to be converted is from the halogen sensor 12, then step 506 actuates the sample and hold circuit 56 wherein the sensor output is stored on capacitor C27 and, further, the sample and hold circuit 56 is disconnected from the operational amplifier 76b so that no change will take place while the A/D converter 54 is effecting the A/D conversion in step 510. In steps 514 and 516, the digital value is serially sent to pin 39 of the microcontroller 62. Thereafter, step 520 tests the D0 and D1 register pair to see if there are any more analog signals to be converted. If there are further signals to be converted, the subroutine 116 again will loop through steps 502 to 524. If not, the subroutine 116 exits to step 522 to return to that point in the program from which the A/D subroutine 116 was called.

Referring now to FIG. 3F, the steps of the watchdog subroutine 104 are further described. When called, the watchdog subroutine 104 enters step 340, which outputs a logic low upon the RD pin 8 of the microcontroller 62 to the operational amplifier 28c of the watchdog circuit 34, whereby a ground circuit is formed for the capacitor C14 of the timing circuit 36; as a result, the capacitor C14 is discharged at least every 32 msec. to prevent the reset circuit 32 from otherwise pulsing the RESET pin 4 of the microcontroller 62 and thus resetting same. Thereafter, the step 342 exits this subroutine 104 to return to that point in the program 100 from which the watchdog subroutine 104 was called.

Figure 4A:
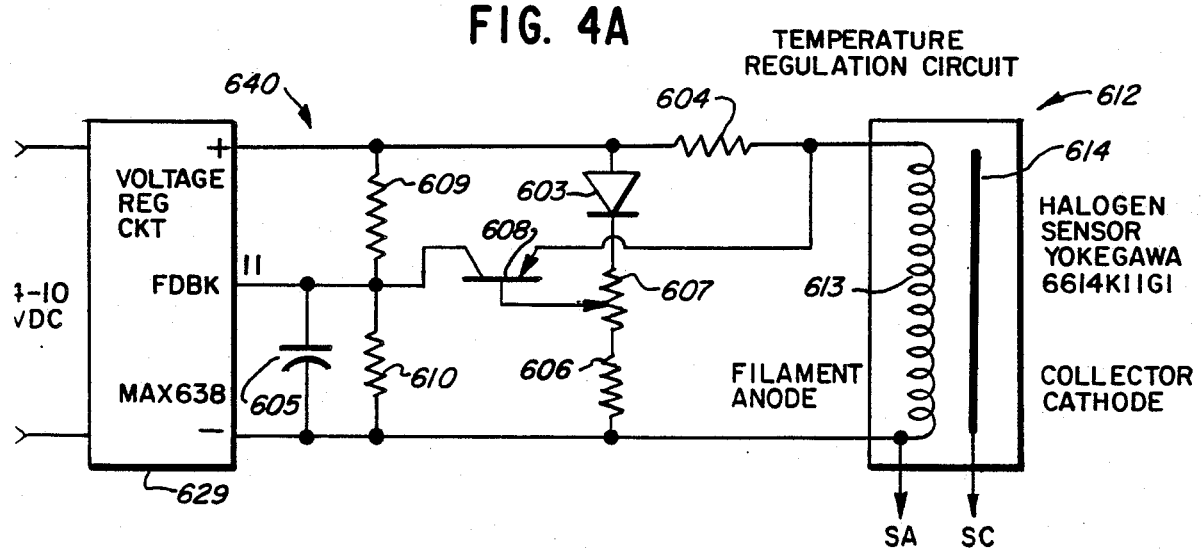
FIGS. 4A and 4B are diagrammatic drawings respectively of a further, preferred embodiment of the halogen sensor and its related temperature regulation circuit, and of the halogen monitoring apparatus as would include a programmed microcontroller and variable gain amplifier.
Figure 4B:
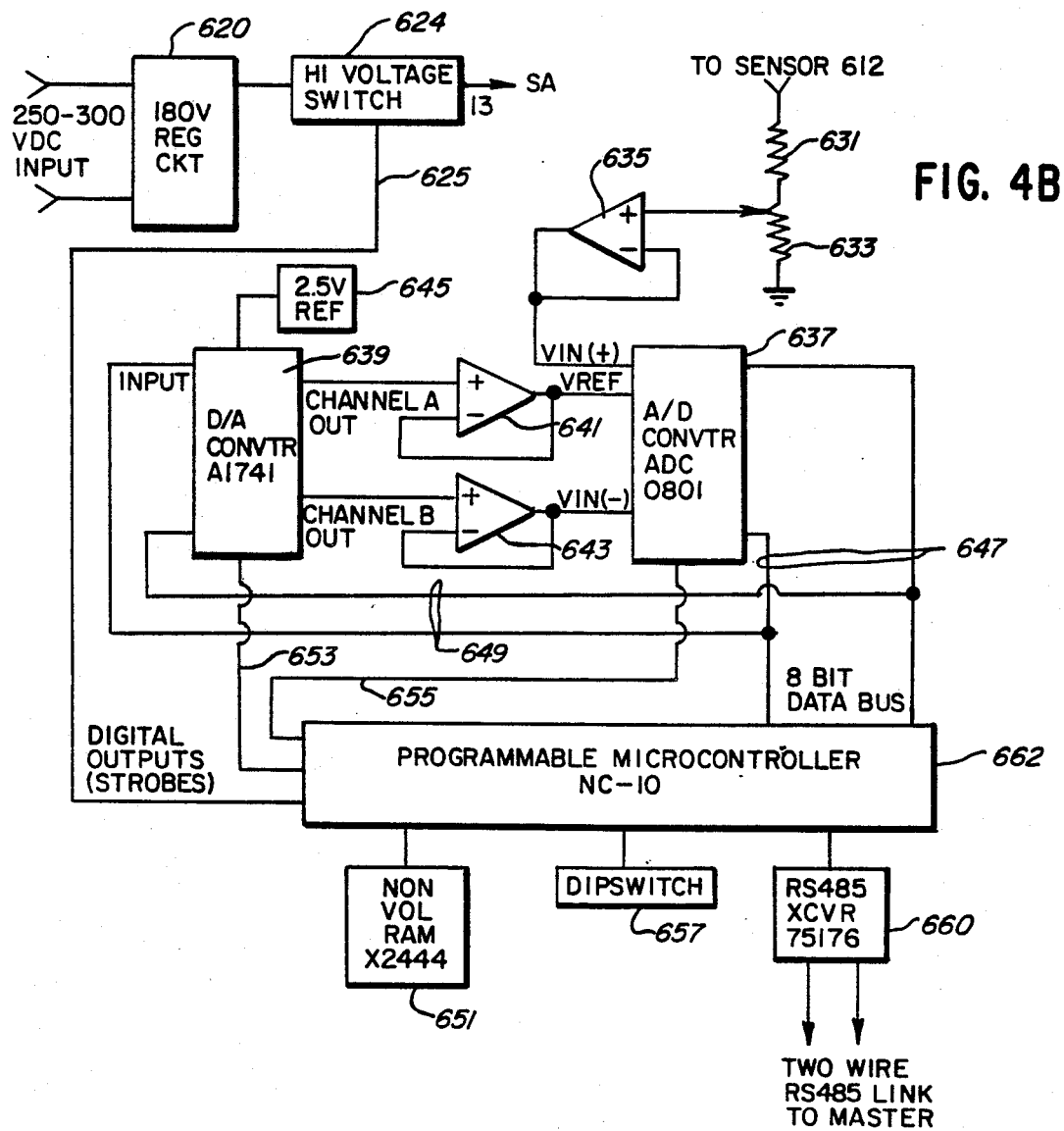

Referring now to FIGS. 4A and 4B, there is shown a further, preferred embodiment of the halogen monitoring apparatus of this invention, wherein like elements are assigned corresponding numbers, but in the 600 series. The sensor 614, as shown particularly in FIG. 4A, is adapted to be incorporated into the halogen monitoring circuit as more fully shown in FIG. 4B. The current flowing through the collector/cathode element 614 is directly proportional to the amount of the halogens in the air sample flowing through the sensor 612 and provides an output signal proportional to that halogen concentration. The power supply 620 provides a regulated 180 volts between the collector/cathode element 614 and the heater/anode element 613. The power control switch 624 is actuated by a signal developed by the microcontroller 662 and applied via the control line 625 to the power control switch 624 to remove the 180 volts across the elements 613 and 614. The switch 624 may take the form either of a series or shunt circuit. The ionization voltage as applied via the switch 624 flows through the heater/anode element 613 to the collector/cathode element 614 and through a series connected resistor 631 and potentiometer 633, as shown in FIG. 4B, to the ground return of the power supply 620.

As shown in FIG. 4A, the voltage applied across the heater/anode element 613 is provided by the heater regulation circuit 640 as comprises a voltage regulator circuit 629, which outputs a substantially fixed voltage which will be regulated in accordance with the temperature changes of the heater/anode element 613 to thereby control the voltage and the current as applied to the element 613 such that a substantially constant temperature of 900° C. is maintained at the heater/anode element 613 of the sensor 612. The heater/anode element 613 is incorporated as a leg of a resistance bridge, which comprises a diode 603, resistors 604 and 606, and a potentiometer 607. If the temperature of the heater/anode element 613 varies, an error current is produced and applied to the base of a transistor 608. The error current is amplified by the transistor 608, which outputs and applies the amplified error current to a feedback input of the voltage regulator circuit 629. The voltage regulator circuit 629 outputs at its + and − terminals the regulated voltage across a pair of resistors 609 and 610, which serve to limit the initial startup voltage. A capacitor 605 is connected in parallel across the resistor 610 and reduces any tendency of this circuit to high frequency oscillation. Typically, the heater/anode element 613 is comprised of a platinum wire. Since the temperature vs. resistance relationship of platinum is consistently linear, the resultant temperature control is carried out without switching effects or variations which would affect the low level ionization currents flowing between the heater/anode element 613 and the collector/cathode element 613. In addition, the temperature regulation circuit 640 does not waste energy in the form of heat, thus significantly extending the reliability and useful life of the components in the circuit 640.

Referring now to FIG. 4B, the output of the sensor 612 is developed by the current as flows through the collector/cathode element 614 and the series connected resistor 631 and potentiometer 633. A voltage proportional to this current is developed at the tap of the potentiometer 633 and is applied to a buffer amplifier 635, which is connected as a voltage follower to the VIN(+) input of an analog-to-digital (A/D) converter 637. The A/D converter 637 provides a digital output via a data bus 647 to an input/output port of the microcontroller 662.

The microcontroller 662 applies a digital output via its input/output port and a data bus 649 to a multichannel digital-to-analog (D/A) converter 639. The microcontroller 662 applies a strobe pulse via a strobe line 653 to the D/A converter 639, which applies via its first or channel A output a reference voltage. After buffering by a voltage follower 641, this reference voltage is applied to the A/D converter 637 at its VREF input. The microcontroller 662 applies a strobe signal via a strobe line 655 to the A/D converter 637, which in response applies via the data bus 647 to the input/output port of the microcontroller 662, a digital signal corresponding to the ratio of the signal applied to the VREF input and the output of the sensor 612 as applied to the VIN(+) input. As will be explained, the microcontroller 662 is programmed for adjusting the level of the VREF input, whereby the gain afforded the output of the sensor 612 is automatically adjusted to be in range without potential stability problems.

As further shown in FIG. 4B, a dipswitch 657 is connected to the microcontroller 662, whereby an operator may throw the dipswitch 657 to cause an offset voltage as developed at a second or channel B output of the D/A converter 639 to be applied to the differential input VIN(−) input of the A/D converter 637, whereby a zero output is applied to the data bus 647. As will explained later, the microcontroller 662 applies via the data bus 649 a digital value to the D/A converter 639 to provide the desired offset after being buffered by a voltage follower 643. As a result, the residual output from the sensor 612 as occurs in the absence of halogens or in the presence of a residual level thereof, is offset to provide a zero input to the input/output port of the microcontroller 662.

Various parameters of the halogen monitoring apparatus as shown in FIG. 4B are stored in a non-volatile memory or RAM 651. Further, the halogen monitoring system and, in particular, its microcontroller 662 is in communication with a master computer, whereby the concentrations of halogen being monitored at the remotely disposed monitoring system may be communicated to the centrally disposed master computer. Further, the master computer can send messages to control and/or reset the operating parameters of the remote halogen monitoring apparatus. In an illustrative embodiment of this invention, a transceiver 660 functions as a two wire serial interface with the master computer using illustratively the Electronic Industries Association Revised Standard 485. In an illustrative embodiment of this invention, the microcontroller 662 may be implemented by that controller as manufactured by the Electronic Monitoring and Controls Corp. under their designation NC-10. The switching voltage regulator 11 may illustratively take the form of that regulator manufactured by Maxim Corp. under their designation MAX638. Illustratively, the A/D converter 637 may take the form of that converter as manufactured under the generic designation ADC 801, the D/A converter 639 may take the form of that converter as manufactured under the generic designation AU 1741 and the transceiver 660 may take the form of that receiver manufactured under the generic designation 75176.

Figure 5A:
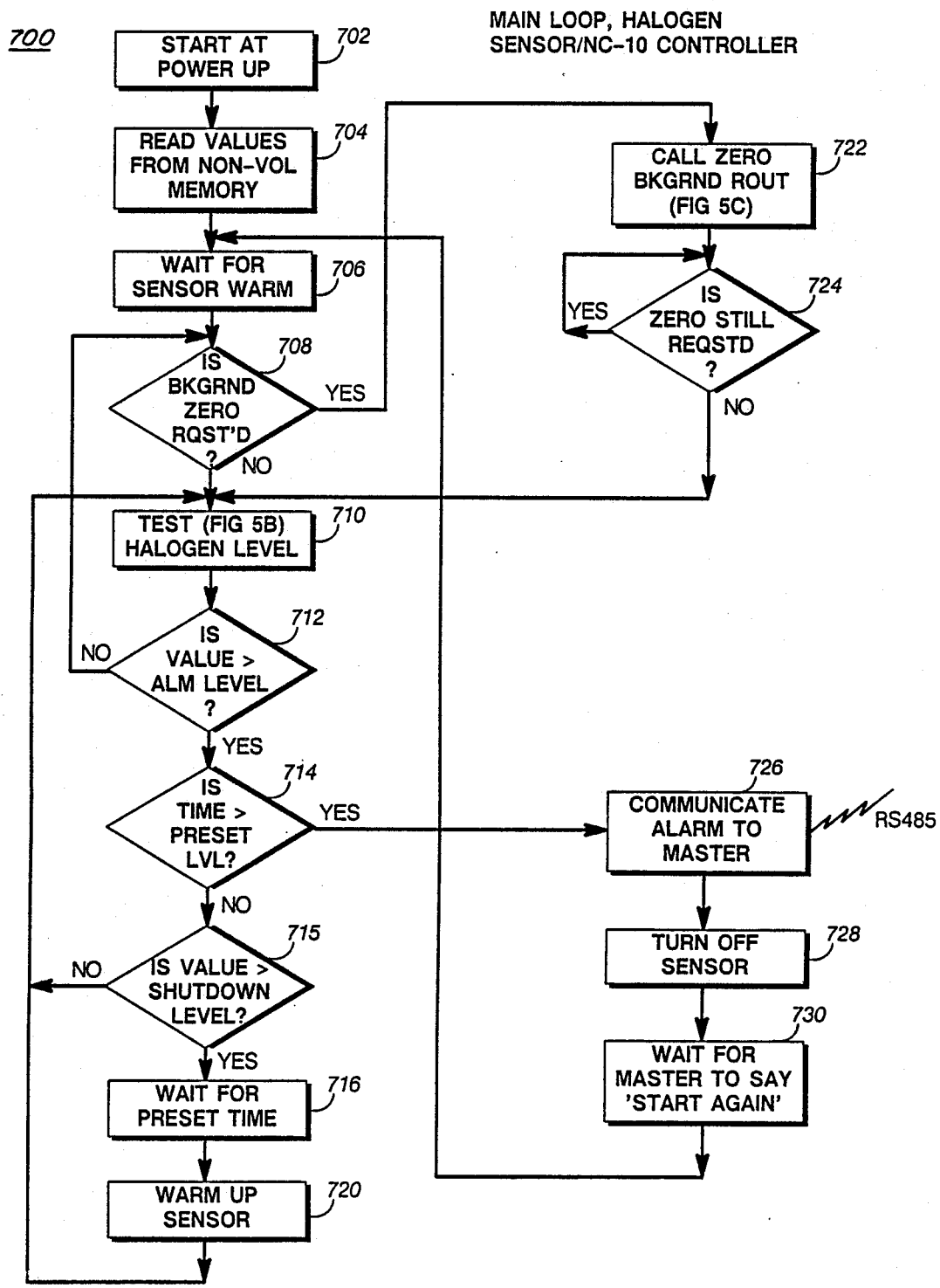
FIGS. 5A to 5C are flow diagrams of the program executed by that microcontroller as shown in FIG. 4B.

Referring now to FIG. 5A, there is shown the main loop of the program 700 as executed by the microcontroller 662. Initially in step 702, the 110 volts AC is applied to the halogen monitoring system of FIGS. 4A and B. Next in step 704, at least three timing parameters and two voltage threshold levels are read out from the non-volatile RAM 651 for later use in the program 700. Illustratively, the three timing parameters include reprogrammable counts indicative of an initial warmup period, a wait period before the cathode/anode voltage is reapplied to the sensor 612 after it has been turned off and an alarm period initiated upon sensing a level of halogen concentration above a first or alarm level thereof. The voltage threshold levels include the alarm level, which if exceeded by the halogen concentration level measured by the sensor 612, will cause an alarm condition, and a shutdown level corresponding to that level, which if exceeded, will cause the sensor 612 to be turned off. These five parameters are reprogrammable and messages may be sent from the master computer to selectively reset any or all of these parameters dependent upon the observed levels of halogen and the particular application of this halogen monitoring apparatus.

Next step 706 times out the initial sensor warmup period to permit the sensor 612 to stabilize. During the warm-up period, the heater/anode element 613 is heated to its operating temperature in the order of 900° C., and the sensor 612 is stabilized before commencing operation of the system and, in particular, the resetting of the microcontroller 662. Then step 708 tests the dipswitch 657 to determine whether or not it has been thrown by the resident operator to adjust the offset voltage, whereby the background level of the output of sensor 612 is determined and is used as an offset such that the output of the A/D converter 637 will provide thereafter a zero output to the microcontroller 662. If yes, the program moves to a subroutine 722 as will be described with respect to FIG. 5C. If not, the main loop moves to step 710, which measures and tests the halogen level as provided by the output signal of the sensor 612, as will explained in more detail with respect to FIG. 5B. Generally, the subroutine 710 adjusts the gain imparted by the A/D converter 637 to the output signal of the sensor 612 so that it is within the range of the A/D converter 637. Next, step 712 determines whether the halogen level as sensed by the sensor 612 is greater than the alarm level. In this regard, the alarm level may be set equal to or less than the shutdown level. As will become apparent, if the measured halogen level exceeds the shutdown level, the anode/cathode voltage will be removed to thereby turn off the sensor 612. On the other hand, if the halogen level exceeds the alarm level, but not the shutdown level, the sensor 612 will be permitted to continue to sense the halogen level at least until the alarm period times out and the sensor 612 is turned off. If the halogen level exceeds the alarm level as determined in step 712, the timing of the preset alarm period will begin and, if exceeded, as determined in step 714, the main loop will move to step 726 to transmit a message via the transceiver 660 to the master computer. Thereafter, step 728 will turn off the sensor 612 until a command "start again" is received from the master computer, at which time the program will return to step 706.

If the alarm period has not timed out as determined in step 714, step 715 determines whether the shutdown level has been exceeded. If not, the main loop continues to monitor the halogen level and returns to step 710. If the shutdown level has been exceeded, the cathode/anode voltage is removed in step 715 from the sensor 612. Next in step 716, the wait period is timed out while the sensor 612 is turned off. Thereafter, step 720 times a second warmup period to permit the sensor 612 to restabilize, before the main loop returns to step 710 to again test the halogen level. Thus, it is seen that if the halogen level exceeds the shutdown level, the sensor 612 will be turned off for the wait period to permit the sensor to recheck the halogen level before sending a communication to the master computer indicative that the shutdown level has been exceeded.

Figure 5B:
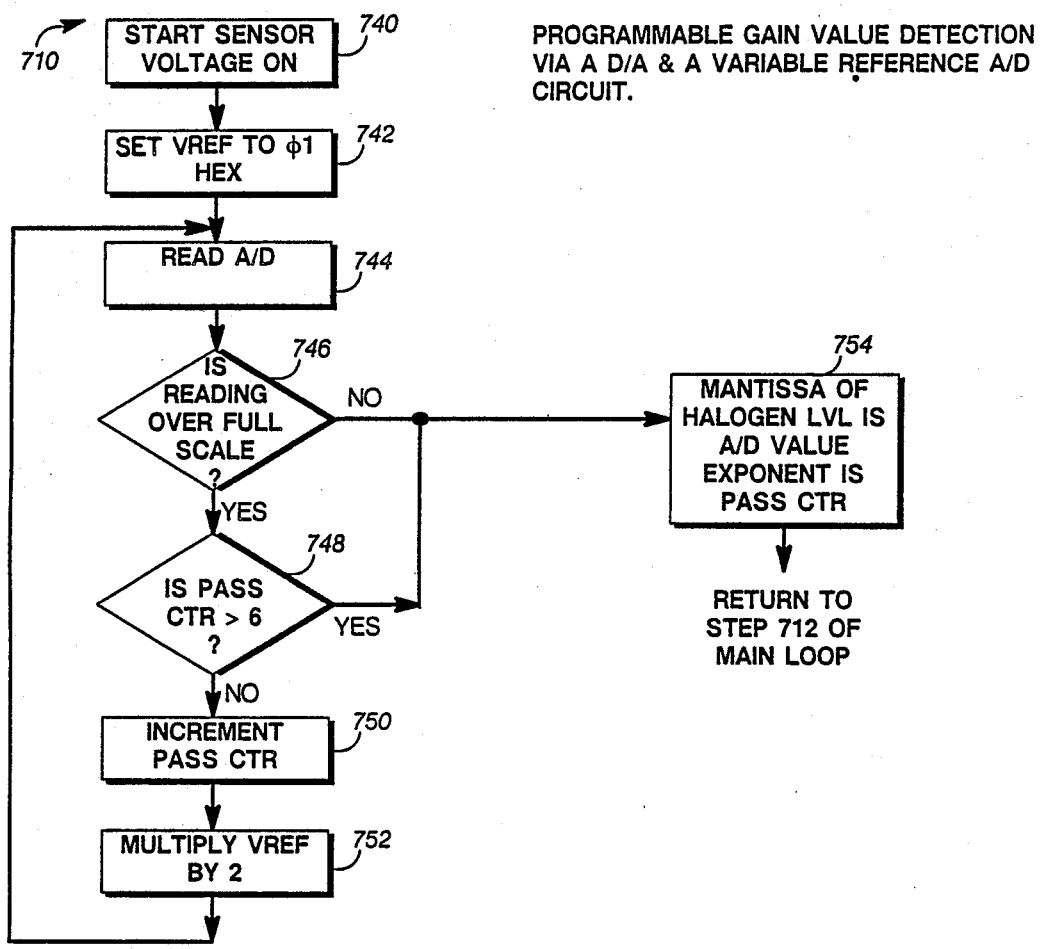

Referring now to FIG. 5B, the halogen level testing subroutine 710 will be more fully explained. The anode/cathode voltage is initially applied to the sensor 712 in step 740, before step 742 causes the microcontroller 662 to apply an 8 bit digital value indicative of the VREF via the data bus 649 to the D/A converter 639, before the microcontroller 662 applies a strobe via the strobe line 653 to cause the corresponding analog value of the VREF to be read out upon its channel A output. The value of the initial digital input is 01 HEX. The digital input to the D/A converter 639 determines that factor by which the voltage output by the voltage reference 645 will be divided to provide an analog signal on the channel A output. In the illustrative example where the reference output is 2.5 V, the initially set voltage on the channel A output equals 2.5/255 V for the digital input of 01 HEX. Next, step 744 causes the microcontroller 662 to apply a strobe via its strobe line 655 to the A/D converter 637 to take a reading of the A/D converter 637. It is understood that this digital reading equals VIN/VREF times 255; thus, if the analog output of the sensor 612 as applied to the VIN(+) input is less than the VREF, the output of the A/D converter 637 will be in range, i.e., less than 255 as determined in step 746.

In particular, step 746 determines whether the digital output of the A/D converter 637 is over full scale, i.e., is equal to 255 or greater. If out of range or over full scale, step 748 determines whether the number of times that the subroutine 710 has incremented a pass counter, i.e., has looped through the steps 744 to 752, exceeds 6. If the number of passes is less than 6, step 750 increments the pass counter, before step 752 multiplies the value of VREF by 2, i.e., the digital output of the microcontroller 662 is increased to 02 HEX and the analog value of VREF appearing upon the channel A output of the D/A converter 639 is doubled. As a result, the effective digital gain imparted by the A/D converter 637 to the sensor signal is doubled. It is seen that the subroutine 710 will loop through the steps 744 to step 752 until the pass counter exceeds 6 or the digital output reading obtained from the A/D converter 637 is in range. If in range, step 754 determines the halogen level as an exponential value, whose mantissa is the output value of the A/D converter 637 and whose exponent is the count accumulated the pass counter. Also, the incremented count of the pass counter corresponds to the gain imparted by the A/D converter 637. After step 754, the program returns to step 712 of the main loop as shown in FIG. 5A. If the pass count exceeds 6 as determined in step 748, the subroutine 710 moves to step 754 to provide an indication that a large halogen reading has been taken.

Figure 5C:
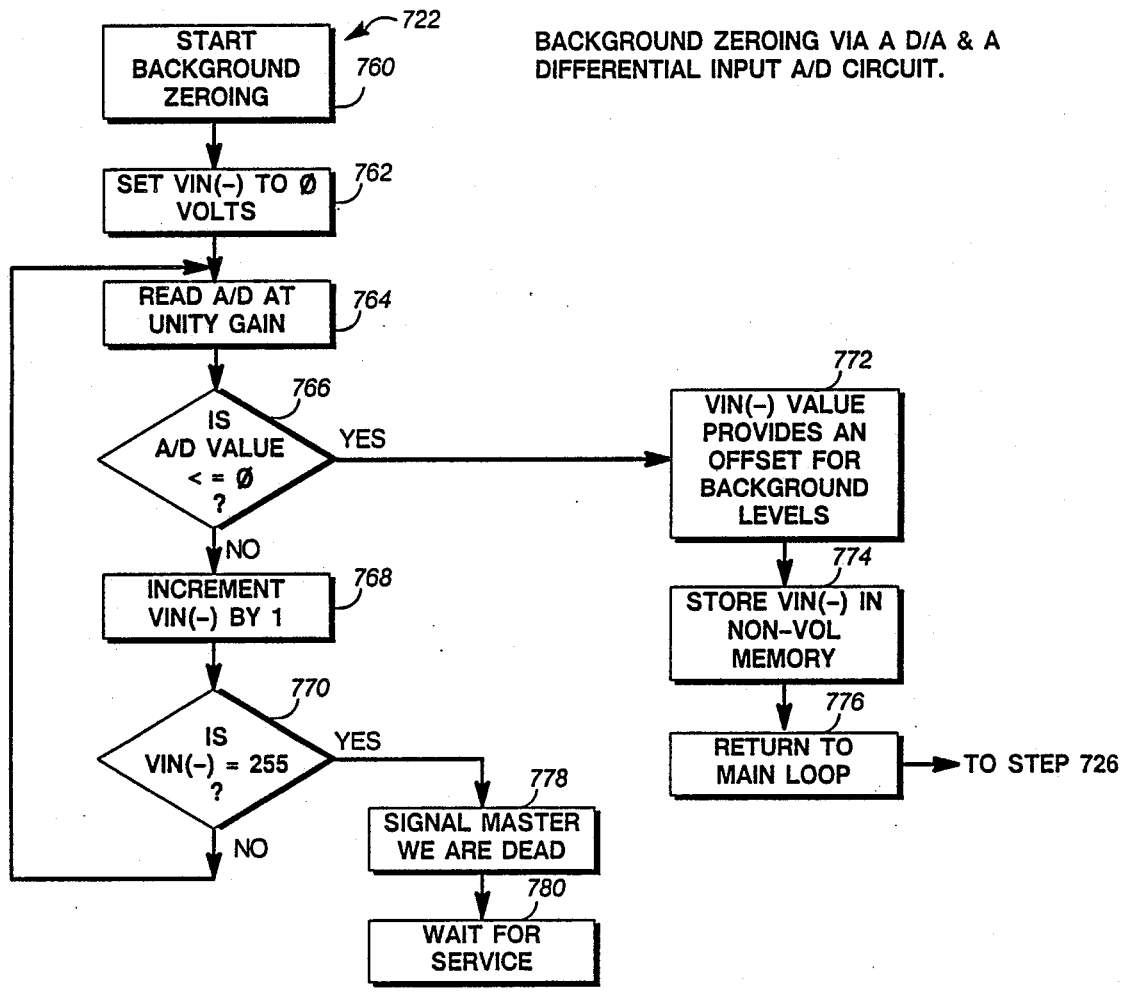

Referring now to FIG. 5C, there is shown the subroutine 722 that is called to zero out the background level of the sensor output as would represent that residual sensor signal in the absence of or with a background level of the halogens in the enclosure being monitored. The subroutine 722 is entered from step 708 to an initial step 760 as would indicate that the dipswitch 657, as shown in FIG. 4B, has been thrown to the corresponding position. In step 762, the microcontroller 662 outputs upon its data bus 649 a digital value corresponding to a 00 HEX and applies a strobe via the strobe line 653 to output from the D/A converter 639 a zero reference signal, which after it is buffered by the voltage follower 643, serves as the offset for the A/D converter 637 at its VIN(−) terminal. Next, step 764 sets the A/D converter 637 to its unity or maximum gain as is designed to provide a max signal, i.e., a digital output indicative of 255. The microcontroller 662 applies a digital value via the data bus 649 to the D/A converter 639 and strobes it via the line 653, whereby an output is provided at channel A. After being buffered by the voltage follower 641, this output serves as the VREF input to achieve unity gain of the A/D converter 637. Next, step 766 examines the output of the A/D converter 637 and, if equal to zero, step 722 stores that value as applied to the VIN(−) input, which provides the desired offset for the background level of halogens sensed by the sensor 612. That offset value is stored in step 774 in the non-volatile RAM 651, before step 776 returns to step 724 of the main loop, as shown in FIG. 5A. Step 724 again tests the dipswitch 657 to determine whether it has been released. If not, the program continues to loop through step 724 until the dipswitch 657 is released, at which time the program returns to step 710.

If the output of the A/D converter 637 is not zero as determined by step 766, step 768 increments by 1 the digital value applied to the D/A converter 639. Thereafter, step 770 determines whether the presently incremented value of VIN(−) equals to 255. Should the VIN(−) value reach 255 without a zero reading, the microcontroller 662 actuates its transceiver 660 to transmit an emergency message to the master computer indicative of detection of an extremely high background level of halogens, before turning off the sensor 612 and waiting in step 780 for service. The subroutine 722 will loop through steps 764 to 770 incrementing the digital value provided by the microcontroller 662 to the D/A converter 639 until a zero reading is obtained in step 766 as indicates that the differential input level as applied to the VIN(−) input would provide a zero reading from the A/D converter 637, whereby the constant background level provided by the sensor 612 is offset or eliminated.

Thus, there has been shown apparatus or a circuit including a sensor for detecting halogen leaks, which is capable of use over an extended period of time in the order of months and even years for monitoring halogen leaks in an enclosure. The apparatus and process of this invention is capable of extending the life of the halogen sensor for extended periods of time by deenergizing this sensor upon the detection of a leak, whereby the continued drawing of the ionization current through the collector/cathode of the sensor is stopped and the life of the sensor extended. Further, the apparatus and process of this invention is capable of initially taking a measurement of the background level of any halogen that may be present in an enclosure, storing that background level over an extended period of time, and subtracting it from the current outputs of the halogen sensor to determine an increase in the levels of concentration of halogen compounds in the enclosure and thus a leak. Further, this invention is capable of operating to sense a wide range of levels of concentration of halogen compounds as may be present in the enclosure, by automatically adjusting the gain of the sensor output amplifier and of and remembering the adjusted gain level and the selected one of a plurality of degrees of sensitivity for this apparatus to determine a valid leak, as opposed to a spurious reading. Because the main controller communicates with this apparatus, the size of the leak, its location, its date and time can be stored onto the memory medium of the main controller for future analysis.

In considering this invention, it should be remembered that the present disclosure is illustrative only and the scope of the invention should be determined by the appended claims.

I claim:

1. Apparatus for detecting an increase of a selected difference in the concentration of halogen gas in a gaseous atmosphere from a first level to a second level thereof, said detecting apparatus comprising:
   (a) a sensor including a heater/anode element and a collector/cathode element disposed to define a space therebetween through which said gaseous atmosphere flows;
   (b) means coupled to said heater/anode element and said collector/cathode element for applying a voltage therebetween, whereby ionization of said halogen gas causes a current flow between said heater/anode element and said collector/cathode element of a magnitude proportional to the concentration level of said halogen gas in said gaseous atmosphere;
   (c) first control means coupled to one of said elements for detecting an increase in said ionization current flow by a corresponding amount as would indicate that the concentration level of halogen gas has increased by said selected difference to provide a manifestation indicative thereof; and
   (d) second control means responsive to said increased current manifestation for controlling said voltage supplying means, whereby its voltage as applied between said heater/anode element and said collector/cathode element is substantially reduced to a magnitude such that said ionization of said halogen gas and thus said current flow between said collector/cathode element and said heater/anode element are extinguished so that the life of said sensor is extended.

2. The detecting apparatus as claimed in claim 1, wherein there is further included means coupled across said heater/anode element for applying a voltage thereacross to produce a current sufficient to heat said sensor to its operating temperature.

3. The detecting apparatus as claimed in claim 1, wherein there is further included alarm means for providing a manifestation indicative of a valid halogen leak, and actuating means responsive to said voltage reduction by said second control means for actuating after a predetermined period of time said voltage applying means to increase said voltage between said heater/anode and collector/cathode elements, whereby said first control means may detect a repeated increase in said ionization current flow in excess of said given difference, said alarm means being responsive to a plurality of said increased current manifestations for providing said valid halogen leak manifestation.

4. The detecting apparatus as claimed in claim 3, wherein said actuating means is also responsive to said increased current manifestation for disabling said first control means.

5. The detecting apparatus as claimed in claim 4, wherein said actuating means causes said voltage applying means to increase said voltage between said heater/anode and collector/cathode elements for a warm-up period, before re-enabling said first control means to detect said ionization current flow, wherein said sensor is permitted to stabilize before said first control means is reenabled to detect a repeated increase in said ionization current flow.

6. The halogen detecting apparatus as claimed in claim 1 as adapted for detecting a leak of said halogen gas within said gaseous atmosphere as confined in an enclosure, said halogen leak detecting apparatus further comprising memory means, and means for taking a first reading of said ionization current flow as indicative of a background level of said halogen gas within said enclosure and for storing said first reading in said memory and for taking second readings of said ionization current flows and for non-destructively accessing said memory and subtracting said first reading from each of said second readings to provide a compensated output indicative of any increase of said level of halogen gas above from said background level.

7. Apparatus for monitoring a gaseous atmosphere within an enclosure over an extended period of time for an increase in the level of concentration of a halogen gas within said enclosure, said gas monitoring apparatus comprising:
   (a) a sensor exposed to said gaseous atmosphere for providing a signal indicative of the level of concentration of said halogen gas within said enclosure;
   (b) memory means;
   (c) first control means for taking an initial reading of said sensor signal as indicative of a background level of the concentration of said halogen gas within said enclosure and for storing said background level in said memory; and
   (d) second control means for thereafter periodically taking current readings of said sensor signal over said extended period of time and for nondestructively accessing said memory means and subtracting said background level from each of said current readings to provide a compensated sensor signal indicative of the current level of halogen concentration less said background level thereof.

8. The monitoring apparatus as claimed in claim 7, wherein said memory means comprises a non-volatile memory.

9. The monitoring apparatus as claimed in claim 8, wherein said non-volatile memory comprises an electrically erasable potentiometer.

10. The halogen monitoring apparatus as claimed in claim 7 as adapted for monitoring said gaseous atmosphere for a given increase in the level of said halogen concentration as would indicate a valid leak of said halogen gas within said enclosure in contrast to a spurious indication thereof, wherein there is further included third control means for initially taking a first reading of said compensated sensor signal and thereafter a second reading of said compensated sensor signal and for storing said first and second readings in a second memory means, fourth control means for accessing said second memory means for determining a difference between said stored first and second readings to provide an indication of said measured increase of the concentration level of said halogen gas, and fifth control means for comparing said measured increase indication with said given increase and, if greater, for providing a warning manifestation indicative of said valid leak of said halogen gas.

11. Apparatus for monitoring a gaseous atmosphere to detect a wide range of the levels of concentration of a halogen gas within said gaseous atmosphere as confined in an enclosure, said monitoring apparatus comprising:
(a) a sensor exposed to said gaseous atmosphere for providing a signal indicative of the concentration level of said halogen gas within said gaseous atmosphere;
(b) means coupled to said sensor for amplifying said sensor signal to output an amplified signal indicative of the halogen gas concentration level, said amplifying means having a variable gain;
(c) means for setting said gain of said amplifying means; and
(d) means coupled to said variable gain amplifying means for determining whether said amplified output signal is greater than a predetermined level and, if so, for causing said gain setting means to decrease said gain of said amplifying means.

12. The halogen gas monitoring apparatus as claimed in claim 11, wherein there is further included means for causing said gain setting means to increase said gain of said amplifying means until said determining means determines that said sensor signal is greater than said predetermined level.

13. The halogen gas monitoring apparatus as claimed in claim 11, wherein said setting means variably sets said gain of said amplifying means at a selected one of a plurality of discrete gains.

14. The halogen gas monitoring apparatus as claimed in claim 13, wherein there is further included means for causing said setting means to increase said gain to the next greater discrete gain of said plurality until said determining means determines that said sensor signal is greater than said predetermined level and, thereafter, for causing said gain setting means to set said gain at the next lower discrete gain of said plurality.

15. The halogen gas monitoring apparatus as claimed in claim 11, wherein said sensor provides its signal in analog form, and there is further included an analog to digital converter coupled to receive said analog sensor signal for converting same into a corresponding digital signal, said determining means responsive to said digital signal for determining whether said analog to digital converter has overflowed and, if so, for causing said setting means to decrease said gain of said amplifying means.

16. The halogen gas monitoring apparatus as claimed in claim 11, as adapted to detect an increase in the level of the concentration of said halogen gas as would indicate a valid leak of said halogen gas as opposed to a spurious indication thereof, wherein said gain setting means increases incrementally said gain until said determining means determines that said sensor signal is greater than said predetermined level and for causing said gain setting means to decrease said gain to a determined lower gain, memory means, means for first taking an original value of said determined gain and thereafter current values of said determined gains and for storing said original value of said determined gain in said memory means, means for accessing said memory means for determining a difference between said original value and each of said current values of said determined gains to provide an indication of the measured increase of the concentration level of said halogen gas, and means for comparing said determined gain difference with a predetermined gain difference and, if greater, for providing a warning indication indicative of said valid leak of said halogen gas.

17. The halogen gas leak monitoring apparatus as claimed in claim 16 wherein said taking means first takes an original value of said sensor signal and thereafter current values of said sensor signal and for storing said original value of said sensor signal in said memory means, and comparing means for comparing said determined gain difference with said predetermined gain increase and if equal and said current value of said sensor signal is greater than said original value of said sensor signal, for providing said warning indication of said valid leak of said halogen gas.

18. The halogen gas monitoring apparatus as claimed in claim 11, wherein there is further included comparison means coupled to said variable gain amplifying means for comparing said amplified output signal with a set reference concentration level and, if said amplified output signal is greater, for providing an indication of a halogen gas leak into said gaseous atmosphere.

19. Apparatus for monitoring a gaseous atmosphere for a selected increase in the level of the concentration of a halogen gas within a given enclosure as would indicate a valid leak of said halogen gas in contrast to a spurious indication, said leak monitoring apparatus comprising:
(a) a sensor exposed to said gaseous atmosphere for providing an output signal indicative of the concentration level of said halogen gas within said enclosure;
(b) means for calibrating said sensor output signal with respect to a background level of the concentration of the halogen gas in said enclosure, to provide a calibrated output signal;
(c) means for periodically taking a reading of said calibrated output signal to provide a series thereof over an extended monitoring period;
(d) means for measuring the difference between successive readings of said calibrated output signal;
(e) means for variably selecting the magnitude of said selected increase and
(f) means for comparing said measured difference with said selected increase and, if greater, for providing an indication of said valid leak of said halogen gas into said enclosure.

20. The monitoring apparatus as claimed in claim 19, wherein said calibrating means comprises a non-volatile memory means means actuated at the beginning of said monitoring period for taking an initial reading of said sensor output signal to provide an indication of said background level of the concentration of said halogen gas within said enclosure and storing same in said non-volatile memory means, and means for non-destructively accessing said non-volatile memory means and subtracting said background level from the current level of said sensor output signal to provide said calibrated output signal.

21. The monitoring apparatus as claimed in claim 19, adapted for transmitting a message indicative of said valid leak indication to a controller disposed remotely of said monitoring apparatus, wherein there is further included means responsive to said indication to be enabled for transmitting said message to the controller.

22. The monitoring apparatus as claimed in claim 21, wherein said transmitting means is responsive to said valid leak indication for transmitting said corresponding measured difference with said message to the controller.

23. The monitoring apparatus as claimed in claim 21, wherein there is included means coupled to said sensor for amplifying said sensor output signal, said amplifying means having a variable gain, means for setting said gain of said amplifying means, means for first taking a first value of said set gain corresponding to said background level of said sensor output signal and thereafter second values of said set gain corresponding to each of said current levels of said sensor output signal and for storing said first and second gain values in said memory means, means for accessing said memory means and for determining a gain difference between said first value and each of said second values of said set gain to provide an indication of said halogen gas, said comparing means comparing said determined gain difference with a predetermined gain difference and, if greater, for providing said leak indication, said transmitting means responsive to said leak indication to be enabled for transmitting said determined gain difference with said message to the controller.

24. Apparatus for detecting and measuring concentration levels of a halogen gas within a gaseous atmosphere over an extended continuum, said continuum comprising a plurality of nonoverlapping ranges, said apparatus comprising:
   (a) a sensor exposed to said gaseous atmosphere for providing a signal indicative of the concentration level of said halogen gas within said gaseous atmosphere;
   (b) means coupled to said sensor for amplifying said sensor signal to output an amplified signal indicative of the halogen gas concentration level, said amplified output signal lying between a first lower and a second upper limit, said amplifying means having a plurality of discrete gains corresponding respectively to said plurality of ranges;
   (c) means for setting said gain of said amplifying means; and
   (d) means coupled to said variable gain amplifying means for determining whether said amplified output signal is greater than said second upper limit and, if so, for causing said gain setting means to decrease said gain of said amplifying means to the next lower discrete gain, whereby said amplified output signal lies between said first and second limits.

25. The halogen gas detecting and measuring apparatus as claimed in claim 24, wherein said amplified output signal is of an analog form, and there is further included means coupled to said amplifying means for receiving and converting said analog output signal into a corresponding digital signal.

26. The halogen gas detecting and measuring apparatus as claimed in claim 24, wherein said gain setting means provides an output signal indicative of said one set discrete gain.

27. The halogen gas detecting and measuring apparatus as claimed in claim 24, wherein said amplified output signal is of an analog form, and there is further included an analog to digital converter for receiving and converting said amplified analog output signal into a corresponding digital output signal, said determining means responsive to said digital output signal for determining whether said analog to digital converter has overflowed and, if so, for causing said gain setting means to set said gain of said amplifying means to the next lower discrete gain.

28. Apparatus for detecting an increase of a selected difference in the concentration of a particular gas in a gaseous atmosphere from a first level to a second level thereof, said detecting apparatus comprising:
   (a) a sensor including a heater/element and a collector/cathode element disposed to define a space therebetween through which said gaseous atmosphere flows:
   (b) first voltage means coupled to said heater/anode element and said collector/cathode element for applying a voltage therebetween to cause a current flow between said elements proportional to the concentration level of said particular gas in said gaseous atmosphere;
   (c) first control means coupled to one of said elements for detecting an increase in said ionization current flow by a corresponding amount as would indicate that the concentration level of halogen gas has increased by said selected difference to provide a manifestation indicative thereof;
   (d) second control means responsive to said increased current manifestation for controlling said first voltage supplying means, whereby its voltage as applied between said heater/anode element and said collector/cathode element is substantially reduced to a level such that said ionization current therebetween is extinguished so that the life of said sensor is extended; and
   (e) second voltage means continuously coupled across said heater/anode element for applying a voltage thereacross to produce a current sufficient to maintain said sensor at its operating temperature.

* * * * *

UNITED STATES PATENT AND TRADEMARK OFFICE
CERTIFICATE OF CORRECTION

PATENT NO. : 4,910,463

DATED : March 20, 1990

INVENTOR(S) : William J. Williams, II, et al.

It is certified that error appears in the above-identified patent and that said Letters Patent is hereby corrected as shown below:

Column 15, line 9, after "7" --(minimum gain)-- is omitted.

Column 18, line 35, "t" should be --to--.

Claim 17, Column 30, line 18, "and" should be --said--.

Claim 23, Column 31, line 25, after "said" (first occurrence) --measured difference in the concentration level of said-- is omitted.

Claim 28, Column 32, line 28, after "/" and before "element" --anode-- is omitted.

Signed and Sealed this

Twenty-ninth Day of September, 1992

Attest:

DOUGLAS B. COMER

*Attesting Officer*   *Acting Commissioner of Patents and Trademarks*